(12) United States Patent
Kobayashi et al.

(10) Patent No.: US 7,953,572 B2
(45) Date of Patent: May 31, 2011

(54) MEASUREMENT SYSTEM, AND PROGRAM PRODUCT FOR MEASUREMENT SYSTEM

(75) Inventors: Toru Kobayashi, Ibaraki (JP); Masao Nakamuro, Takarazuka (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 284 days.

(21) Appl. No.: 11/904,392

(22) Filed: Sep. 27, 2007

(65) Prior Publication Data

US 2008/0082287 A1    Apr. 3, 2008

(30) Foreign Application Priority Data

Sep. 29, 2006   (JP) ................................. 2006-266494

(51) Int. Cl.
G06F 15/00    (2006.01)

(52) U.S. Cl. ........ 702/127; 345/419; 345/420; 345/421; 345/422; 345/423; 382/154

(58) Field of Classification Search ............... 702/58, 702/150, 152, 155–159; 345/419–422, 423; 382/154

See application file for complete search history.

(56) References Cited

U.S. PATENT DOCUMENTS

| | | | |
|---|---|---|---|
| 5,469,563 A | 11/1995 | Morita | 395/183.01 |
| 5,862,252 A * | 1/1999 | Yamamoto et al. | 382/154 |
| 6,585,340 B1 * | 7/2003 | Borrell | 347/14 |
| 6,891,625 B2 | 5/2005 | Tomita et al. | 356/601 |
| 7,027,641 B2 | 4/2006 | Ide et al. | 382/154 |
| 7,453,609 B2 * | 11/2008 | Itagaki | 358/518 |
| 7,454,054 B2 * | 11/2008 | Fukumoto | 382/154 |
| 7,457,545 B2 * | 11/2008 | Wirth et al. | 398/119 |
| 7,508,961 B2 * | 3/2009 | Chen et al. | 382/118 |
| 7,529,006 B2 * | 5/2009 | Itagaki et al. | 358/519 |
| 7,545,536 B2 * | 6/2009 | Hayashi | 358/1.9 |
| 2001/0012016 A1 * | 8/2001 | Ide et al. | 345/582 |
| 2002/0118274 A1 * | 8/2002 | Yahashi | 348/46 |
| 2002/0163623 A1 * | 11/2002 | Hirohara et al. | 351/212 |
| 2003/0094108 A1 * | 5/2003 | Shiki | 101/171 |

(Continued)

FOREIGN PATENT DOCUMENTS

JP    6-50779 A    2/1994

(Continued)

OTHER PUBLICATIONS

Japanese "Notice of Reasons for Rejection" dated Apr. 7, 2009 for counterpart Japanese Application No. 2006-266494; together with an English-language translation thereof.

(Continued)

*Primary Examiner* — Carol S Tsai
(74) *Attorney, Agent, or Firm* — Sidley Austin LLP

(57) ABSTRACT

A measurement system for obtaining a predetermined estimated value, including a measuring section for acquiring measurement data with respect to a measurement object, a display section for displaying indication concerning a measurement, a display controller, a measurement controller, a storing section for storing the measurement data, a computing section for obtaining the estimated value based on the measurement data, and a checking section for checking whether a required number of measurement data has been acquired. The display controller causes the display section to display first information relating to measurement elements required for acquiring the measurement data, and second information, for allowing an operator to recognize whether the measurement has been completed. The measurement controller causes the selection information to function as a site for accepting a command indicating start of the measurement of the measurement element relating to the individual selection information.

14 Claims, 14 Drawing Sheets

U.S. PATENT DOCUMENTS

| | | | |
|---|---|---|---|
| 2004/0133107 A1* | 7/2004 | Hashimoto | 600/437 |
| 2005/0087022 A1* | 4/2005 | Yokono | 73/818 |
| 2005/0249400 A1* | 11/2005 | Fukumoto | 382/154 |

FOREIGN PATENT DOCUMENTS

| | | |
|---|---|---|
| JP | 6-323909 A | 11/1994 |
| JP | 2001-183108 A | 7/2001 |
| JP | 2002-296008 A | 10/2002 |
| JP | 2003-28676 A | 1/2003 |
| JP | 2003-66079 A | 3/2003 |
| JP | 2003-197143 A | 7/2003 |
| JP | 2004-12192 A | 1/2004 |
| JP | 2004-245819 A | 9/2004 |
| JP | 2005-61926 A | 3/2005 |

OTHER PUBLICATIONS

Japanese "Notice of Reasons for Rejection" dated Sep. 30, 2008 for counterpart Japanese Application No. 2006-266494; Together with an English-language translation thereof.

* cited by examiner

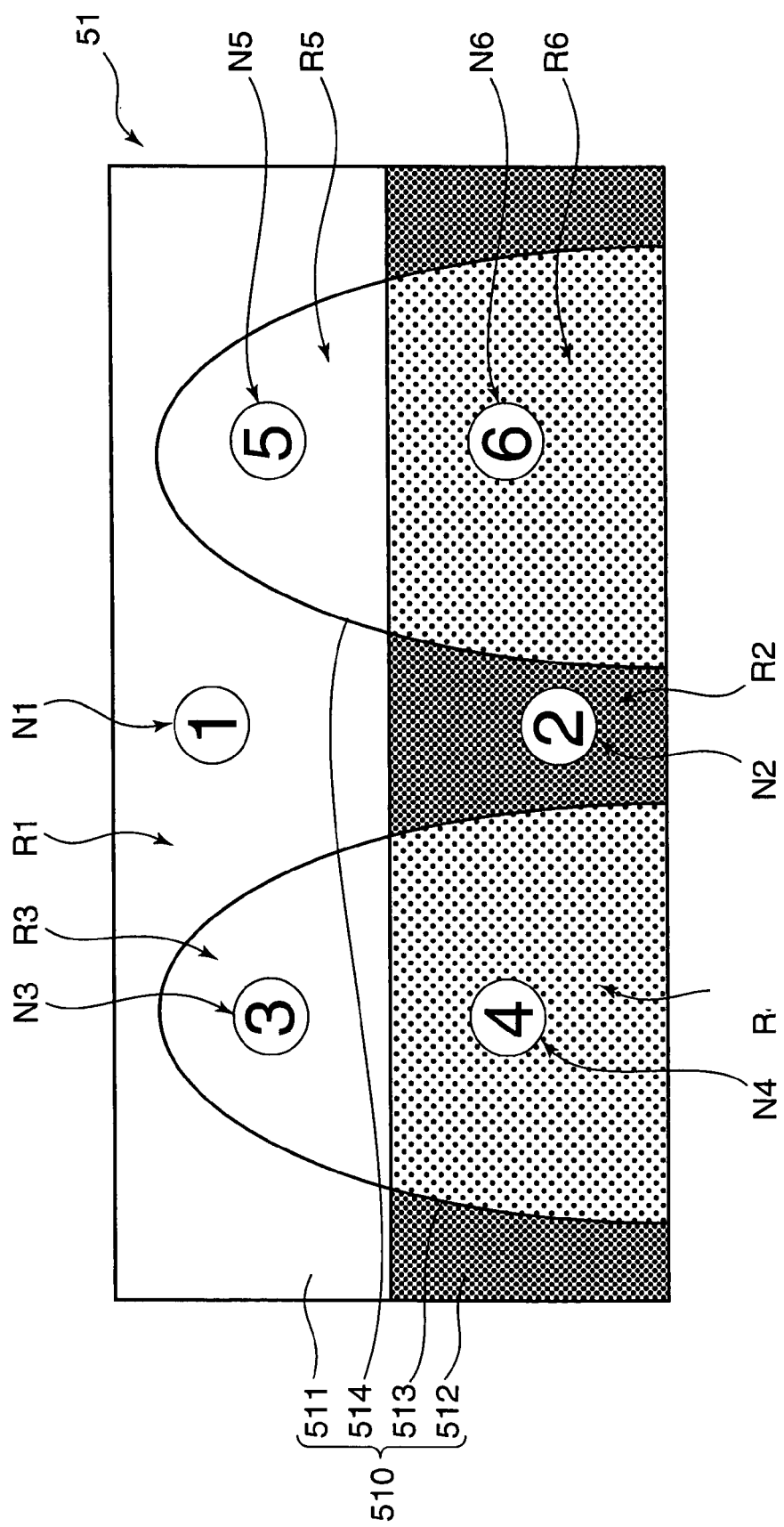

MEASUREMENT SYSTEM, AND PROGRAM PRODUCT FOR MEASUREMENT SYSTEM

This application is based on Japanese Patent Application No. 2006-266494 filed on Sep. 29, 2006, the contents of which are hereby incorporated by reference.

BACKGROUND OF THE INVENTION

1. Field of the Invention

The present invention relates to a measurement system for obtaining a predetermined estimated value with use of multiple measurement data whose measurement positions, measurement objects, measurement conditions, or the like are different from each other, and a program product for the measurement system.

2. Description of the Related Art

In the case where measurement data for plural measurement elements such as measurement positions, measurement objects, or measurement conditions are acquired, and a predetermined estimated value is calculated with use of the multiple measurement data, an operator may be required to manually perform a measuring operation for each of the measurement elements, collect the acquired measurement data, and perform calculation to obtain the predetermined estimated value. In this case, the operator has to rely on his or her memory in judging whether the measurement of the measurement element has been completed or not. As a result, the operation efficiency may be lowered because the operator performs duplicate measurements of the same measurement element, or an operation error such as measurement skip may occur. In addition, the operator is required to record the correlation between the measurement elements and the measurement data, which may also lower the operation efficiency.

There is known a system for supporting a measuring operation requiring measurement of multiple measurement elements, as disclosed in Japanese Unexamined Patent Publication No. 2003-28676 (D1). The system disclosed in D1 is directed to support a measuring operation, wherein plural measurement positions are defined as measurement elements. Specifically, the system is operated in such a manner that a screen prompting an operator to select a targeted measurement position is displayed on a display monitor so that the operator is allowed to select the targeted measurement position and perform a measuring operation at the selected measurement position, whereby measurement data at the selected measurement position is acquired for storage.

The system disclosed in D1 is directed to display the measurement position on the display monitor and store the measurement data acquired at the selected measurement position. In other words, the system is designed to easily and securely collect multiple measurement data. In the system recited in D1, since it is necessary to calculate a targeted estimated value based on the collected measurement data, the system does not significantly contribute to improvement on the operation efficiency in obtaining the estimated value. As a conclusion, the system recited in D1 does not provide sufficient support for an operation of calculating a predetermined estimated value with use of multiple measurement data, based on a premise that a required number of measurement data are acquired.

SUMMARY OF THE INVENTION

In view of the above problems residing in the conventional examples, it is an object of the invention to provide a measurement system that enables to support a measuring operation of obtaining a predetermined estimated value, using a required number of measurement data whose measurement elements are different from each other, and sufficiently enhance the operation efficiency, and a program product for the measurement system.

A measurement system according to an aspect of the invention that has accomplished the object is a measurement system for obtaining a predetermined estimated value by using multiple measurement data. The measurement system includes: a measuring section for performing a predetermined measurement with respect to a measurement object to acquire measurement data; a display section for displaying indication concerning a measurement; a display controller for causing the display section to display first information relating to a plurality of measurement elements of the measurement object required for acquiring the multiple measurement data, the first information including individual selection information relating to the measurement elements, and second information to be displayed in association with the selection information for allowing an operator to recognize whether measurement of the corresponding measurement element has been completed; a measurement controller for performing a measurement start control of causing the individual selection information to function as a site for accepting a command indicating start of the measurement of the corresponding measurement element relating to the individual selection information, and generating a control signal to cause a measuring section to perform the measurement in response to receiving the command, a measurement execution control of causing the measuring section to perform the measurement of the selected measurement element, and a measurement completion display control of causing the display section to display whether the measurement has been completed in association with the selection information; a storing section for storing the measurement data acquired by the measurement in association with the measurement element; a computing section for reading the multiple measurement data from the storing section to compute the estimated value; and a checking section for checking whether the measurement data required for the computation has been acquired in computing the estimated value by the computing section.

A program product according to another aspect of the invention is a program product for operating a measurement system, provided with a display section, a storing section, and a data processor, to obtain a predetermined estimated value by performing a predetermined measurement with respect to a measurement object and using a required number of measurement data acquired by the measurement. The program product includes: a program which causes the data processor to execute: a process of causing the display section to display image information representing an image of the measurement object in a state that selection information for allowing an operator to visually recognize a plurality of measurement elements of the measurement object for which the measurement is to be performed is included, and display a discernible indicator, to be displayed in association with the selection information, for allowing the operator to recognize whether the measurement has been completed; a process of functioning each of the selection information to be displayed on the display section as a site for accepting a command indicating start of the measurement of the corresponding measurement element relating to the individual selection information, and generating a control signal to cause a measuring section to perform the measurement in response to receiving the command; a process of causing the discernible indicator of the measurement element for which the measurement has been completed to display that the measurement has been completed; a process of causing the storing section to store the measurement data acquired by the measurement in association with information for specifying the measurement element; a process of reading the measurement data from the storing section to perform computation to obtain the estimated value; a process of determining whether a predetermined number of measurement data required for the computation has been acquired in obtaining the estimated value; and a process of causing the display section to display the estimated value obtained by the computation; and a medium for recording the program.

These and other objects, features and advantages of the present invention will become more apparent upon reading the following detailed description along with the accompanying drawing.

BRIEF DESCRIPTION OF THE DRAWINGS

FIG. 6 is a plan view enlargedly showing an image of a sample to be displayed on a graphic display portion.

DETAILED DESCRIPTION OF THE PREFERRED EMBODIMENTS

Figure 1:
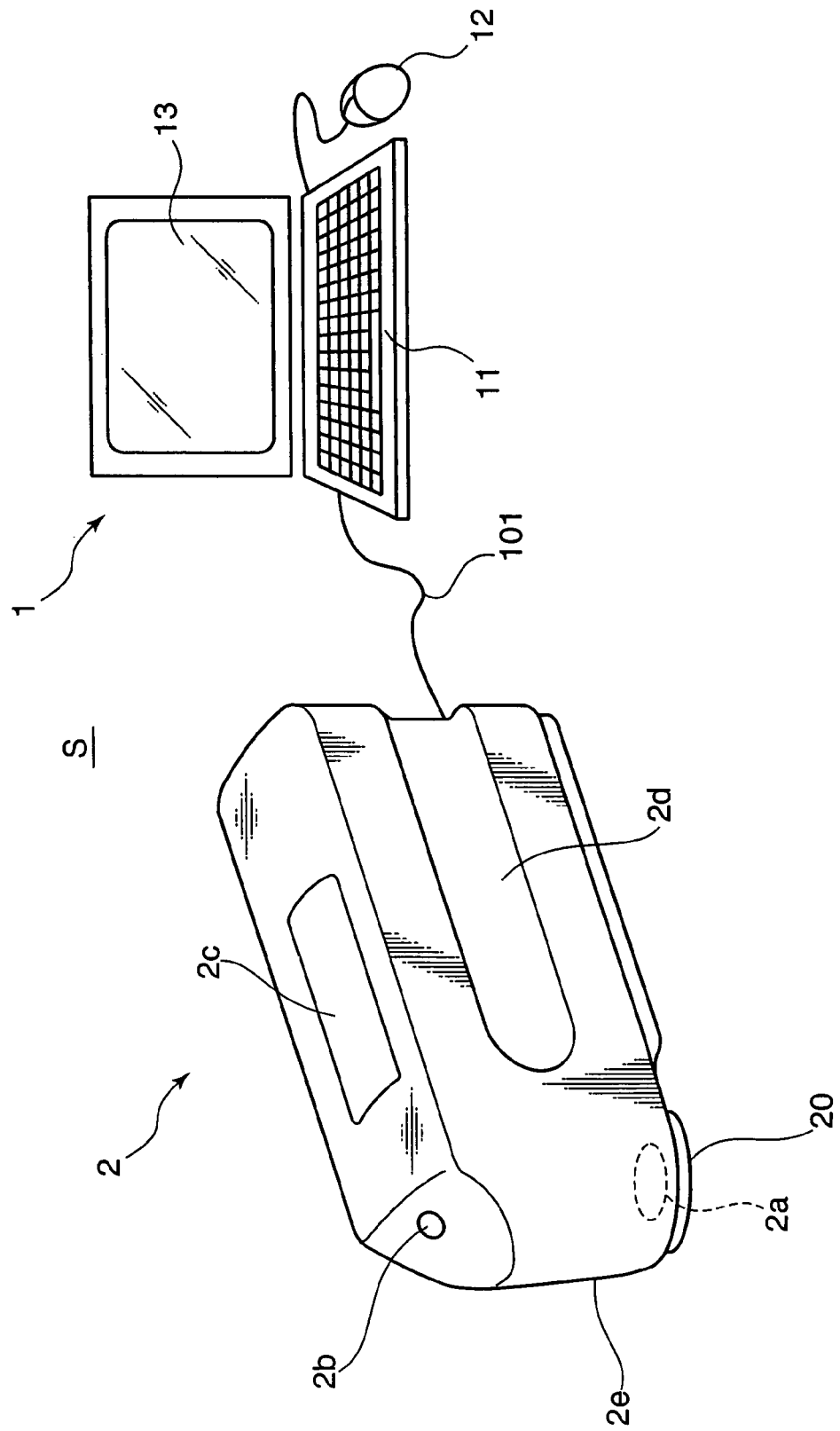
FIG. 1 is a diagram showing a hardware configuration of a measurement system embodying the invention.

In the following, an embodiment of the invention is described referring to the drawings. An example of measuring the color of a sample is described as the embodiment of the invention.

FIG. 1 is a diagram showing a hardware configuration of a measurement system embodying the invention. The measurement system S includes a personal computer 1 and a multi-angle spectrophotometer 2 as a measuring section, and is configured in such a manner that the personal computer 1 and the multi-angle spectrophotometer 2 are connected to each other via a signal cable 101. The personal computer 1 has a main body 11 equipped with a data processing function, a data storing function, and the like, an operating section 12 as a selector, and a display section 13. The computer main body 11 has a display controller, a measurement controller, a storing section, a computing section, and a checking section.

The spectrophotometer 2 projects inspection light onto a measurement object, and receives reflected light from the measurement object to obtain spectral intensity data of the received inspection light. The spectrophotometer 2 is formed in its entirety into a longitudinal box-shaped casing body 2e, as a casing member. Various components including a multi-angle illumination system and light receiving system for projecting/receiving inspection light are housed in the casing body 2e. A bottom wall of the casing body 2e serves as a measurement aperture surface 20. A measurement aperture 2a of a proper shape e.g. an elliptical shape is formed in the measurement aperture surface 20.

The casing body 2e further includes a viewfinder 2b through which an operator is allowed to view a surface of a sample, as a measurement object, a display section 2c which is arranged on a top part of the casing body 2e and is constituted of e.g. LCD to display a measurement result or the like, and a grip portion 2d which is easily grippable by the operator for handling the spectrophotometer 2. In performing a measuring operation, the operator directs the measurement aperture 2a opposite to the measurement object, activates the illumination system and light receiving system to project/receive inspection light.

Figure 2:
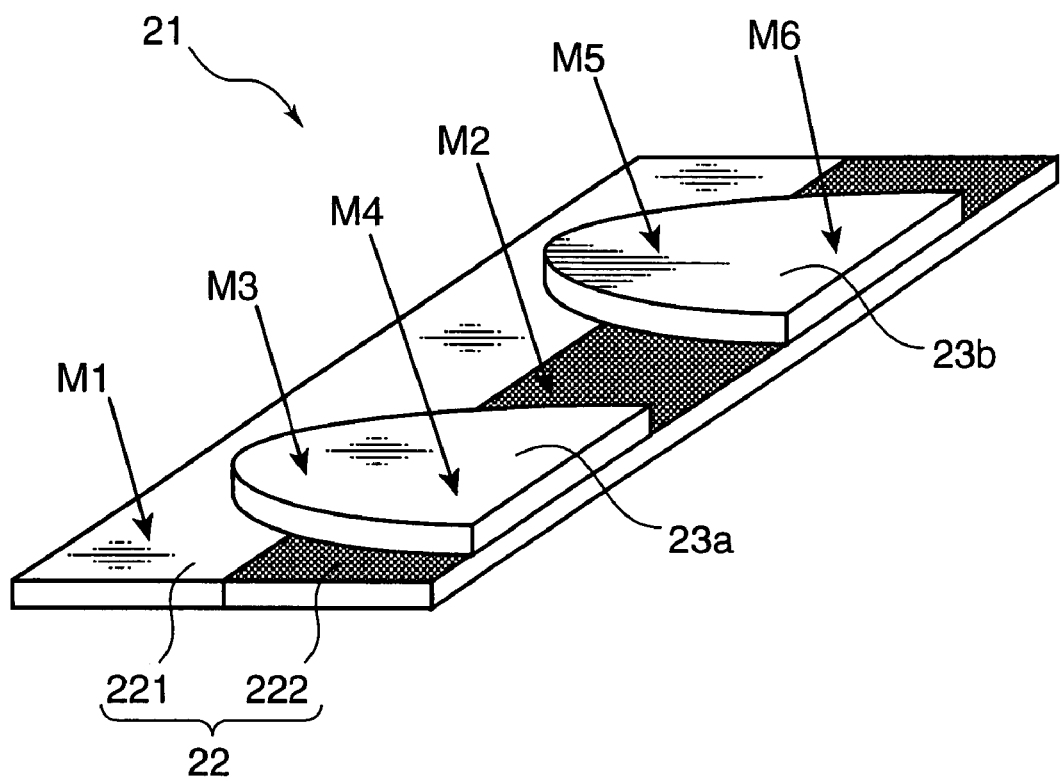
FIG. 2 is a perspective view showing an example of a sample to be used in assessing the quality of a paint or a pigment.

The spectrophotometer 2 is suitably used in assessing the quality of a paint or a pigment. FIG. 2 is a perspective view showing an example of a sample 21 (also called as "tomobiki" sample) to be used in assessing the quality of a paint or a pigment. The sample 21 is obtained by coating layers 23a and 23b of a paint (pigment) on a surface of a base plate 22, where a white background portion 221 and a black background portion 222 are formed half-and-half. Each of the paint layers 23a and 23b is coated continuously on the white background portion 221 and the black background portion 222. Generally, the paint layer 23a serves as a standard sample, and the paint layer 23b serves as a comparison sample.

The paint layer 23a and the paint layer 23b of the sample 21 are disposed as opposed to the measurement aperture 2a of the spectrophotometer 2 to assess the quality e.g. the color of the sample 21. Then, measurement data i.e. spectral intensity data is acquired by projecting/receiving inspection light. Specific measurement sites of the sample 21 are, as indicated by the arrows M1, M2, M3, M4, M5, and M6 in FIG. 2, a measurement site M1 on the white background portion 221, a measurement site M2 on the black background portion 222, a measurement site M3 on the white background portion 221 where the paint layer 23a is coated, a measurement site M4 on the black background portion 222 where the paint layer 23a is coated, a measurement site M5 on the white background portion 221 where the paint layer 23b is coated, and a measurement site M6 on the black background portion 222 where the paint layer 23b is coated. Estimated values such as a K/S value (rating index of light absorption and scattering), a tinting power, or a hiding power are acquired by using all the measurement data for the six measurement sites indicated by the arrows M1 through M6.

In assessing the quality of a paint or a pigment, an estimated value is calculated by conducting multiple measuring operations under different measurement conditions and acquiring multiple measurement data. Therefore, during the process of assessing the quality of the sample, an operation step may be dropped, or mismatching between condition and measurement value may occur. There is proposed an idea of fixing the measurement order in order to prevent drop of an operation step. Fixing the measurement order, however, may lower the operation efficiency. The measurement system of the embodiment is designed to eliminate the aforementioned drawbacks.

In the embodiment, the measurement system S is constituted of the spectrophotometer 2 and the personal computer 1. However, the hardware configuration of the measurement system S is flexibly designed. For instance, the spectrophotometer 2 may be provided with a data processing function, a data storing function, and the like of the personal computer 1. In other words, the components of the measurement system S may be integrally mounted in the casing body 2e of the spectrophotometer 2. In the modification, since the measurement system S can be provided in such a manner that the components of the measurement system S are integrally mounted in the spectrophotometer 2, the measurement system S is provided with superior handling performance or portability.

Figure 3:
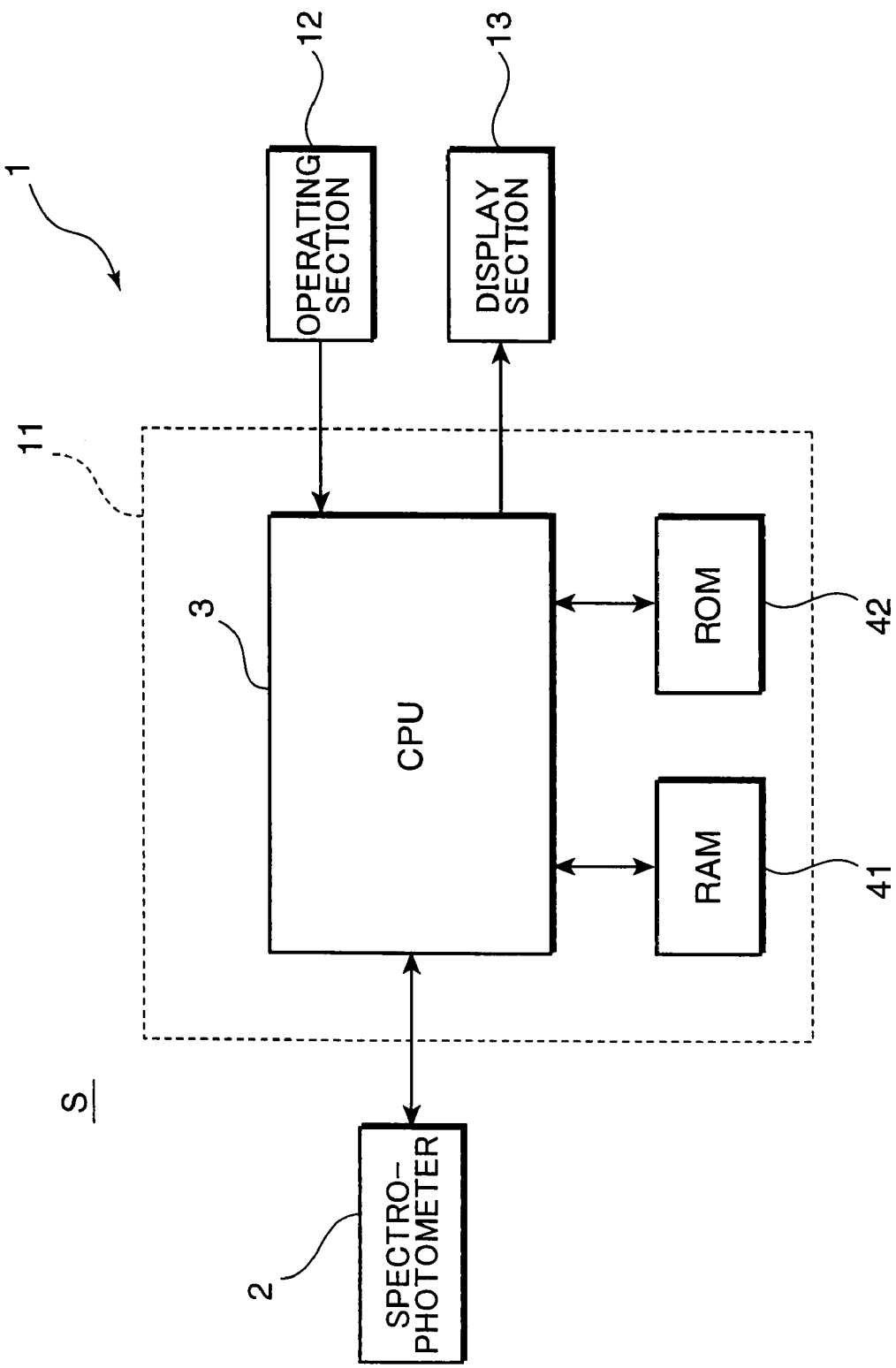
FIG. 3 is a block diagram schematically showing an electric configuration of the measurement system shown in FIG. 1.

FIG. 3 is a block diagram schematically showing an electric configuration of the measurement system S i.e. the personal computer 1 shown in FIG. 1. As mentioned above, the personal computer 1 has the computer main body 11, the operating section 12, and the display section 13. The computer main body 11 controls a measurement operation of the spectrophotometer 2, and performs computation to obtain a predetermined estimated value based on the measurement data acquired by the spectrophotometer 2. The computer main body 11 includes an RAM (Random Access Memory) 41 for temporarily storing measurement data, computation data, or the like, an ROM (Read Only Memory) 42 for storing various control programs or the like, and a CPU (Central Processing Unit) 3 for reading the control program or the like from the ROM for execution. The functional parts of the computer main body 11 will be described later in detail referring to FIG. 4.

The operating section 12 includes a mouse to be connected to the computer main body 11, and is adapted to supply a command signal to the computer main body 11 or the spectrophotometer 2 to cause the computer main body 11 or the spectrophotometer 2 to perform a predetermined processing or a measuring operation. In particular, in this embodiment, the operator is allowed to select a measurement area based on graphical indication as image information of the measurement object i.e. the sample 21 to be displayed on the display section 13. A keyboard, a touch panel or a like instrument may serve as the operating section 12, in place of the mouse.

The display section 13 is adapted to display various indications concerning a color measurement. For instance, the display section 13 is constituted of an LCD (Liquid Crystal Display), a CRT (Cathode Ray Tube), or a plasma display device. In this embodiment, the display section 13 displays a graphic image of the measurement object in a state that measurement areas for color measurement are visually divided, measurement data concerning color measurement, an estimated value to be obtained based on the measurement data, and the like.

Figure 4:
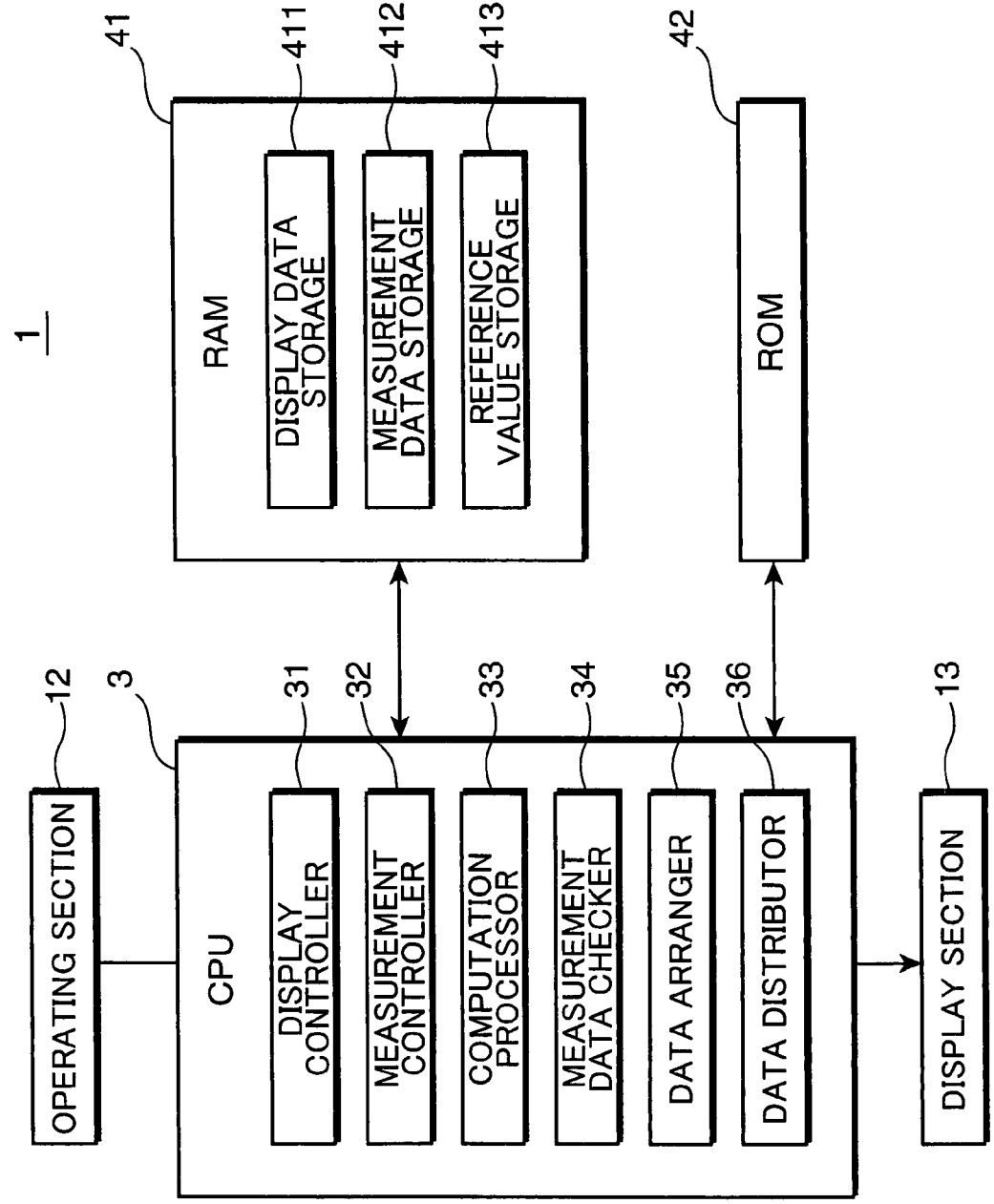
FIG. 4 is a functional block diagram showing a detailed arrangement of functional parts of a personal computer to be used in the embodiment.

FIG. 4 is a functional block diagram showing a detailed arrangement of the functional parts of the personal computer 1. The CPU 3 functionally includes a display controller 31, a measurement controller 32, a computation processor 33 as a computing section, a measurement data checker 34 as a checking section, a data arranger 35, and a data distributor 36 as a determining section. The RAM 41 includes a display data storage 411, a measurement data storage 412, and a reference value storage 413.

The display controller 31 causes the display section 13 to display image information, as first information, which relates to the sample 21, in a state that selection information is included. The selection information is adapted to allow the operator to visually recognize multiple measurement elements of the sample 21 for which measurement is to be performed. The display controller 31 also causes the display section 13 to display discernible indicators, as second information, in association with the selection information, for allowing the operator to recognize whether the measurement for the targeted measurement element has been completed. The display data is stored in the display data storage 411 in the RAM 41. The display controller 31 is operative to retrieve display data according to needs for displaying the retrieved data on the display section 13.

Figure 5:
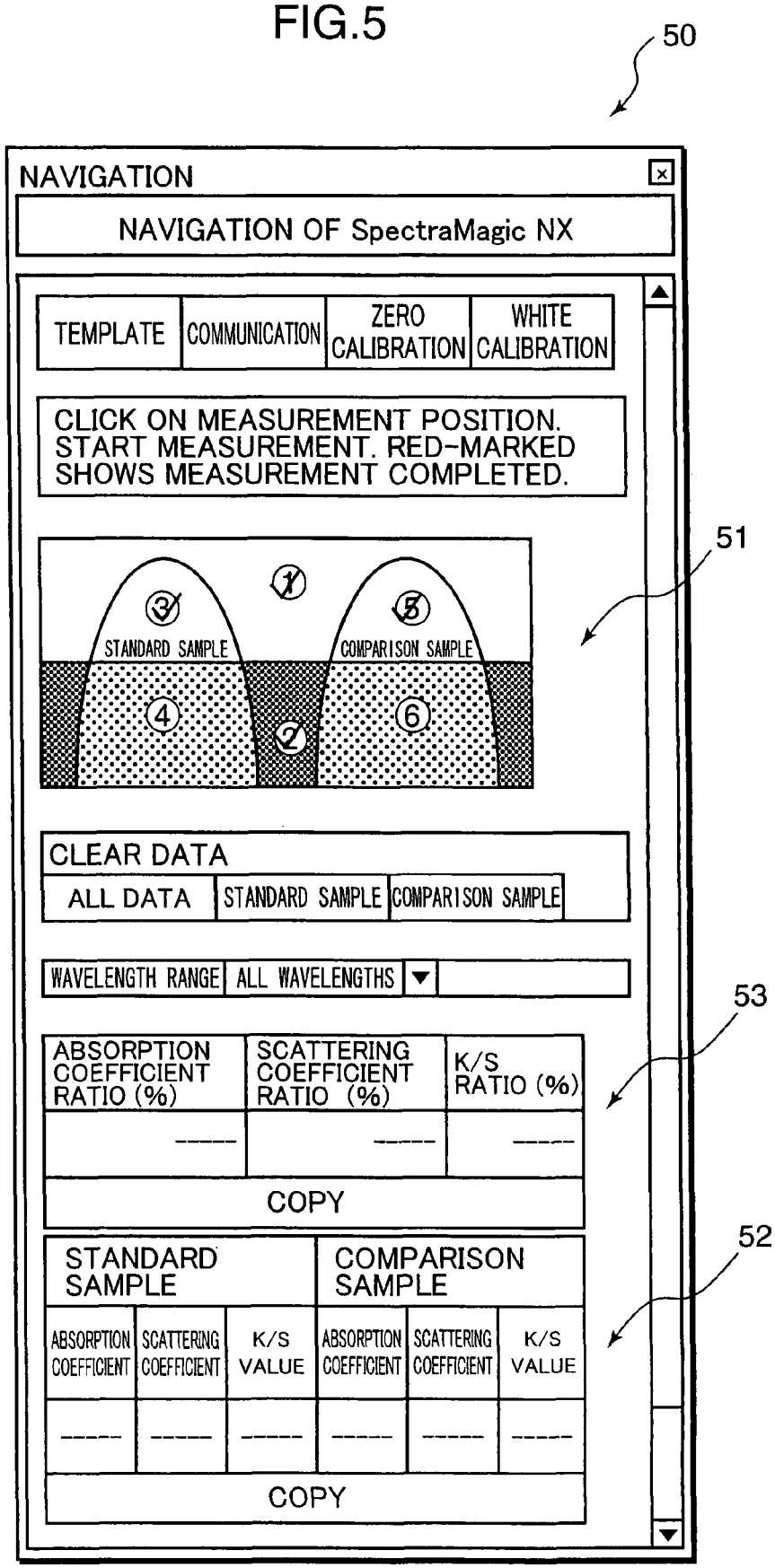
FIG. 5 is a plan view showing a measurement navigation screen, as an example of a screen image to be displayed on a display section.

FIG. 5 is a plan view showing a measurement navigation screen 50, as an example of a screen image to be displayed on the display section 13 by the display controller 31. The measurement navigation screen 50 includes a graphic display portion 51, a measurement data display portion 52, and an estimated value display portion 53. On the graphic display portion 51, a photographic image, as a plan view image of a measurement plane of the sample 21, a color drawing image or a deformed image simulating the sample 21, or a like image is displayed in a state that measurement areas i.e. measurement elements for color measurement are visually divided. On the measurement data display portion 52, measurement data or computed data acquired for each of the measurement areas of the sample 21 are individually displayed as numerical data. On the estimated value display portion 53, an estimated value of the color of the sample 21 obtained based on the measurement data is displayed as numerical data.

FIG. 6 is a plan view enlargedly showing a measurement object image 510 of the sample 21 to be displayed on the graphic display portion 51. The measurement object image 510 includes a white portion 511 corresponding to the white background portion 221 of the sample 21 shown in FIG. 2, a black portion 512 corresponding to the black background portion 222, a first coated portion 513 corresponding to the paint layer 23a as a standard sample, and a second coated portion 514 corresponding to the paint layer 23b as a comparison sample. The contours defining the portions 511 through 514 are displayed in a visually recognizable manner.

With the above indication control, the measurement object image 510 is visually divided into six measurement areas. Specifically, the measurement object image 510 is visually divided into a first measurement area R1 corresponding to the white portion 511 devoid of the paint layers 23a and 23b, a second measurement area R2 (in the example of FIG. 6, the second measurement area R2 is provided at three sites) corresponding to the black portion 512 devoid of the paint layers 23a and 23b, a third measurement area R3 corresponding to the white portion 511 on which the paint layer 23a as a standard sample is coated, a fourth measurement area R4 corresponding to the black portion 512 on which the paint layer 23a is coated, a fifth measurement area R5 corresponding to the white portion 511 on which the paint layer 23b as a comparison sample is coated, and a sixth measurement area R6 corresponding to the black portion 512 on which the paint layer 23b is coated.

The first through the sixth measurement areas R1 through R6 correspond to the actual measurement sites indicated by the arrows M1 through M6 in FIG. 2. The first through the sixth measurement areas R1 through R6 serve as selection information for allowing the operator to visually recognize the measurement elements (in this embodiment, the measurement positions) of the sample 21 for which the measurement is to be performed. Alternatively, a button image describing the measurement contents may be used as selection information, which will be described later in detail referring to FIG. 13, in place of using the divided measurement areas on the image of the sample 21.

The encircled numbers "1" through "6" are allocated to the first through the sixth measurement areas R1 through R6, respectively. The elements indicated by the encircled numbers "1" through "6" are discernible indicators N1, N2, N3, N4, N5, and N6 which are displayed in association with the first through the sixth measurement areas R1 through R6 to allow the operator to recognize whether the measurement of a targeted measurement area has been completed. In this example, an encircled number is attached to each of the measurement areas, as a discernible indicator. Alternatively, identifiers such as numerals/characters including Roman numerals, "hirakana", "katakana", Chinese numerals, and alphabets; various symbols; pictograms; or the like may be allocated alone or in combination of two or more.

The measurement data display portion 52 is provided with columns in which an absorption coefficient, a scattering coefficient, and a K/S value are displayed with respect to each of the standard sample and the comparison sample. The parameters of the standard sample are calculated based on spectral reflectance measurement data with respect to the first through the fourth measurement areas R1 through R4, and the parameters of the comparison sample are calculated based on spectral reflectance measurement data with respect to the first measurement area R1, the second measurement area R2, the fifth measurement area R5, and the sixth measurement area R6. The estimated value display portion 53 is provided with columns in which an absorption coefficient ratio, a scattering coefficient ratio, and a K/S ratio are displayed. These estimated values are calculated based on the absorption coefficients, the scattering coefficients, and the K/S values of the standard sample and the comparison sample.

Referring back to FIG. 4, the measurement controller 32 performs a measurement start control of functioning each of the first through the sixth measurement areas R1 through R6 of the measurement object image 510 to be displayed on the graphic display portion 51 as a site for accepting a command indicating start of color measurement for the corresponding measurement area. Then, in response to receiving a command indicating start of color measurement for one of the first through the sixth measurement areas R1 through R6 from the operating section 12, the measurement controller 32 performs a measurement execution control of causing the spectrophotometer 2 to execute measurement for the targeted measurement area. For instance, when the operator points an intended area of the first through the sixth measurement areas R1 through R6 for which the measurement is to be performed, with a pointer of the mouse, and clicks on the pointed area, the measurement controller 32 controls the spectrophotometer 2 to start a measuring operation.

The operator shifts the measurement aperture 2a (see FIG. 1) of the spectrophotometer 2 to such a position as oppose to the targeted measurement site of the sample 21 before giving a command to start color measurement. For instance, in measuring the color of the third measurement area R3, the operator grips the grip portion 2d of the spectrophotometer 2, and directs the measurement aperture 2a as opposed to the site indicated by the arrow M3 of the sample 21 shown in FIG. 2. Then, the operator points the third measurement area R3 with the mouse pointer, and clicks thereon to start color measurement of the third measurement area R3.

Figure 7A:
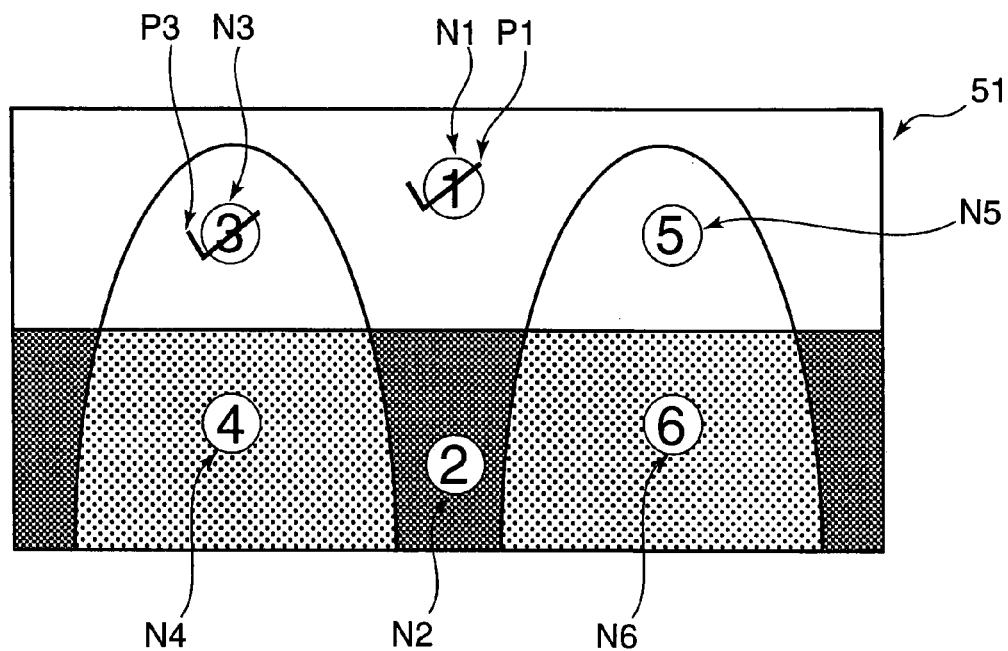
FIGS. 7A and 7B are plan views each showing an example of a screen image showing that measurement has been completed.
Figure 7B:
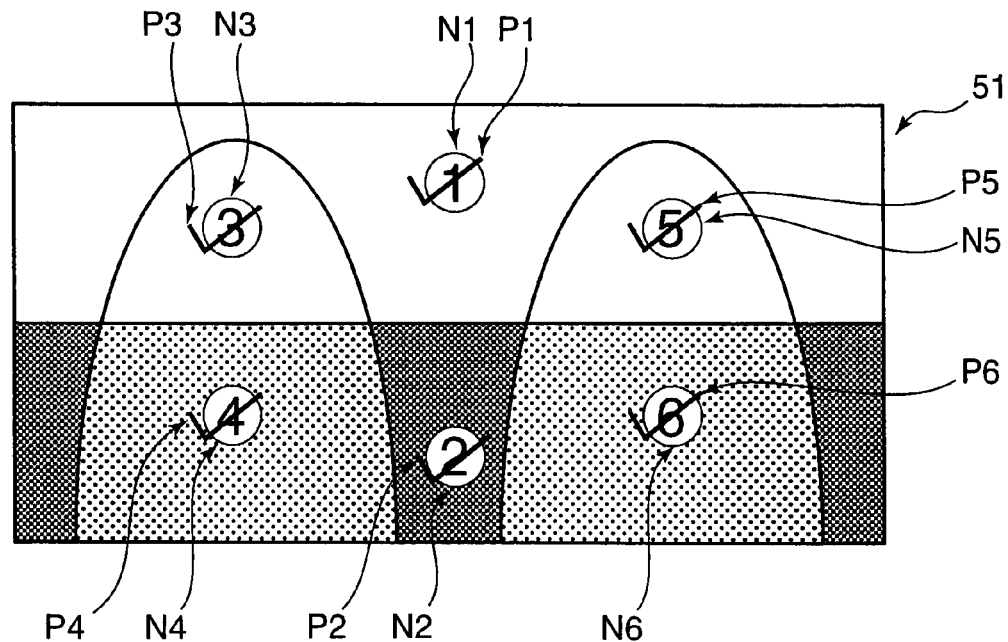

The measurement controller 32 performs a measurement completion display control of causing one of the discernible indicators N1 through N6 to be displayed in association with the targeted measurement area where the measurement has been completed to display that the measurement has been completed. FIGS. 7A and 7B each shows an example showing that the measurement has been completed. In the examples, a check mark "✓" as additive information is superimposedly displayed on the discernible indicators N1 through N6. The check mark "✓" is merely an example of the additive information. Alternatively, a character, a symbol, a pictogram, or a like indication equivalent to the check mark "✓" may be displayed in a superimposed manner. Further alternatively, the discernible indicator indicating that the measurement has been completed may be displayed in a different color or may be caused to blink.

FIG. 7A shows that measurement completion indications P1 and P3 are superimposedly displayed on the discernible indicators N1 of the first measurement area R1 and the discernible indicator N3 of the third measurement area R3, respectively. This indication status shows that measurements of the first measurement area R1 and the third measurement area R3 have been completed. On the other hand, FIG. 7B shows that measurement completion indications P1, P2, P3, P4, P5, and P6 are superimposedly displayed on all the discernible indicators N1 through N6 of the first through the sixth measurement areas R1 through R6. This indication status shows that all the measurements for the first through the sixth measurement areas R1 through R6 have been completed.

With the above indication control, the operator can check the progress of measurement, irrespective of the measurement order of the measurement elements. This enables to suppress duplicate measurements of the same measurement area, or measurement skip. Thus, the operator is allowed to flexibly set the measurement order according to his or her convenience, while securing measurement latitude, and prevent measurement error.

The measurement controller 32 is operative to receive measurement data from the spectrophotometer 2, and write the measurement data into the measurement data storage 412 in the RAM 41. In this operation, the measurement controller 32 is operative to attach identification information capable of specifying the measurement area from which the measurement data has been derived, to the measurement data, based on a measurement start command signal which has been issued to one of the first through the sixth measurement areas R1 through R6, and record the measurement data into the measurement data storage 412 by correlating the measurement area and the measurement data.

The computation processor 33 reads the measurement data from the measurement data storage 412, and performs computation to obtain a predetermined estimated value based on the measurement data. The computation result is displayed on the display section 13. The computation processing to be executed by the computation processor 33 is initiated in response to issuance of a computation start command signal from the measurement data checker 34 to be described below.

The measurement data checker 34 judges whether multiple measurement data required for computation have been acquired in obtaining an estimated value or the like by the computation processor 33. If it is judged that a predetermined number of measurement data required for computation have been acquired, the measurement data checker 34 generates a computation start command signal, and causes the computation processor 33 to execute a predetermined computation.

More specifically, in the embodiment, after spectral reflectance measurement data for the first through the fourth measurement areas R1 through R4 have been acquired, parameters of the paint layer 23a as a standard sample such as a light absorption coefficient, a scattering coefficient, or a K/S value can be computed. Upon confirming that the measurement data for the four measurement areas R1 through R4 have been acquired, the measurement data checker 34 generates a computation start command signal indicative of starting computation of the parameters of the standard sample, and causes the computation processor 33 to automatically start computation to obtain the parameters. The computation results are displayed on the columns (see FIG. 5) relating to the standard sample in the measurement data display portion 52. Upon confirming that spectral reflectance measurement data for the first measurement area R1, the second measurement area R2, the fifth measurement area R5, and the sixth measurement area R6 have been acquired, the measurement data checker 34 generates a computation start command signal indicating start of computation of the parameters of the comparison sample, and causes the computation processor 33 to automatically start computation to obtain the parameters. The computation results are displayed on the columns (see FIG. 5) relating to the comparison sample in the measurement data display portion 52.

After all the spectral reflectance measurement data for the first through the sixth measurement areas R1 through R6 are acquired, it is possible to obtain an absorption coefficient ratio, a scattering coefficient ratio, and a K/S ratio, as estimated values of the comparison sample. Thus, upon confirming that measurement data for the six measurement areas R1 through R6 have been acquired, the measurement data checker 34 generates a computation start command signal indicative of starting computation to obtain the estimated values of the comparison sample, and causes the computation processor 33 to execute a predetermined computation. The computation results are displayed in the corresponding columns (see FIG. 5) on the estimated value display portion 53. Thus, the estimated values are automatically derived, without the operator's giving a computation start command. This enables to efficiently perform the measuring operation.

The data arranger 35 has a function of selectively erasing the measurement data stored in the measurement data storage 412. Specifically, in response to issuance of a certain operation command e.g. a pre-notice indicating that the measurement is continued from the operating section 12 to one of the first through the sixth measurement areas R1 through R6 of the measurement object image 510 displayed on the display section 13, the data arranger 35 erases the measurement data obtained in relation to the measurement area from the measurement data storage 412. In response to the erasing operation, the measurement controller 32 changes the measurement completion indication (in this embodiment, indicated by the check mark "✓") which is displayed superimposedly on one of the discernible indicators N1 through N6 indicating the measurement area corresponding to the erased measurement data, into a measurement incompletion indication (in this embodiment, the check mark "✓" is cleared).

The function of the data arranger 35 is activated to expedite the measuring operation in the case where measurement objects of the same configuration are sequentially measured multiple times. In the case where color measurement is completed for one sample 21, as shown in FIG. 7B, an image that the measurement completion indications P1 through P6 are superimposedly displayed on all the discernible indicators N1 through N6 is displayed on the graphic display portion 51. Also, the measurement data for the first through the sixth measurement areas R1 through R6 are stored in the measurement data storage 412. If color measurement of another sample 21 having the same configuration as the preceding sample 21 is performed, following the color measurement of the preceding sample 21, it is often the case that at least the measurement data for the first measurement area R1 and the second measurement area R2 corresponding to the white background portion 221 and the black background portion 222 are commonly used. In such a case, measuring the first through the sixth measurement areas R1 through R6 all over again for the succeeding sample 21 is not desirable in the aspect of efficiency.

In view of the above, for instance, in response to receiving a command from the operating section 12 indicating that the third through the sixth measurement areas R3 through R6 are selected for sequential measurement, the data arranger 35 erases the measurement data that have been acquired for the third through the sixth measurement areas R3 through R6 in the preceding measurement from the measurement data storage 412. Then, the measurement controller 32 clears the measurement completion indications P3 through P6 in the discernible indicators N3 through N6 which are displayed in association with the third through the sixth measurement areas R3 through R6. Thereby, the operator is allowed to clearly recognize the site for the succeeding measurement by way of the discernible indicators N3 through N6 in performing color measurement of the succeeding sample 21 whose configuration is the same as that of the preceding sample 21. In this arrangement, there is no likelihood that the measurement data for the preceding sample 21 may be used in obtaining an estimated value for the succeeding sample 21.

The data arranger 35 is operative to read correlation information representing correlation between the first through the sixth measurement areas R1 through R6. In response to receiving a command indicating that one of the correlated measurement areas has been selected, the data arranger 35 erases the measurement data corresponding to the other measurement area(s) correlated with the selected measurement area from the measurement data storage 412, as well as the measurement data corresponding to the selected measurement area.

Figure 8:
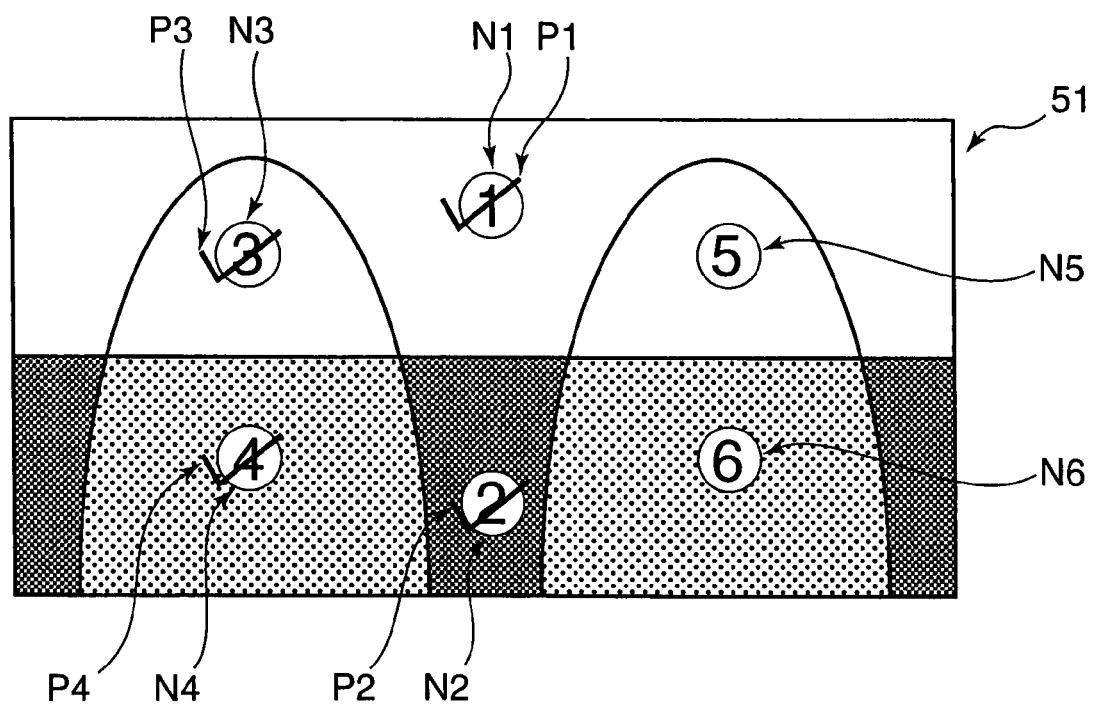
FIG. 8 is a plan view for describing a function of a data arranger.

In this embodiment, since the third and the fourth measurement areas R3 and R4, and the fifth and the sixth measurement areas R5 and R6 are the areas where the same paint is coated, respectively, the third and the fourth measurement areas R3 and R4, and the fifth and the sixth measurement areas R5 and R6 are the correlated measurement areas, respectively. Accordingly, as shown in FIG. 8, for instance, in the case where the fifth measurement area R5 as a first measurement element is selected as an area for sequential measurement, the data arranger 35 erases the measurement data corresponding to the sixth measurement area R6, as a second measurement element, which is correlated with the fifth measurement area R5 from the measurement data storage 412, as well as the measurement data corresponding to the fifth measurement area R5. A similar operation as mentioned above is performed in the case where the sixth measurement area R6 is selected. Then, the measurement controller 32 clears the measurement completion indications P5 and P6 in the discernible indicators N5 and N6 which are displayed in association with the fifth and the sixth measurement areas R5 and R6. If there is stored correlation information showing that the third through the sixth measurement areas R3 through R6 are correlated with each other, in response to receiving a command indicating that one of the third through the sixth measurement areas R3 through R6 has been selected, the measurement data corresponding to the third through the sixth measurement areas R3 through R6 including the selected measurement area are erased from the measurement data storage 412. Thus, the operation efficiency is further enhanced.

The data distributor 36 determines the measurement area from which the measurement data has been derived, based on adequacy of the measurement data acquired by the spectrophotometer 2, and a value of the actual measurement data. This operation is performed to allow the measurement data obtained by the actual measurement to be written into the measurement data storage 412, as data corresponding to the actually measured site, if the measurement area selected by the operator on the measurement object image 510 and the measurement site actually measured by the spectrophotometer 2 are not coincident.

The data distributor 36 compares a range of values of the measurement data which is supposed to be obtained, with a measurement data value actually acquired by the spectrophotometer 2 for each of the first through the sixth measurement areas R1 through R6, and determines the measurement area from which the measurement data has been derived. The measurement data value which is supposed to be obtained is stored in the reference value storage 413 in the RAM 41, as a distribution reference value for the measurement data. The distribution reference value is a numeric value in a range which is normally expected to be obtained from the color of the measurement object, and is empirically defined.

The data distributor 36 reads the distribution reference value from the reference value storage 413, determines the measurement area corresponding to the acquired measurement data, and revises the identification information to be attached to the measurement data in writing the measurement data into the measurement data storage 412, if the determined measurement area is not coincident with the measurement area to which a measurement start command has been given from the operator. If the acquired measurement data does not correspond to any of the measurement areas, the data distributor 36 judges that matching error has occurred, and causes the display section 13 to display an error message. Providing the data distributor 36 having the above function is advantageous in preventing likelihood that the measurement data may be stored in the measurement data storage 412 in a state that the measurement data is associated with the measurement area which should not be associated with the measurement data.

Figure 9:
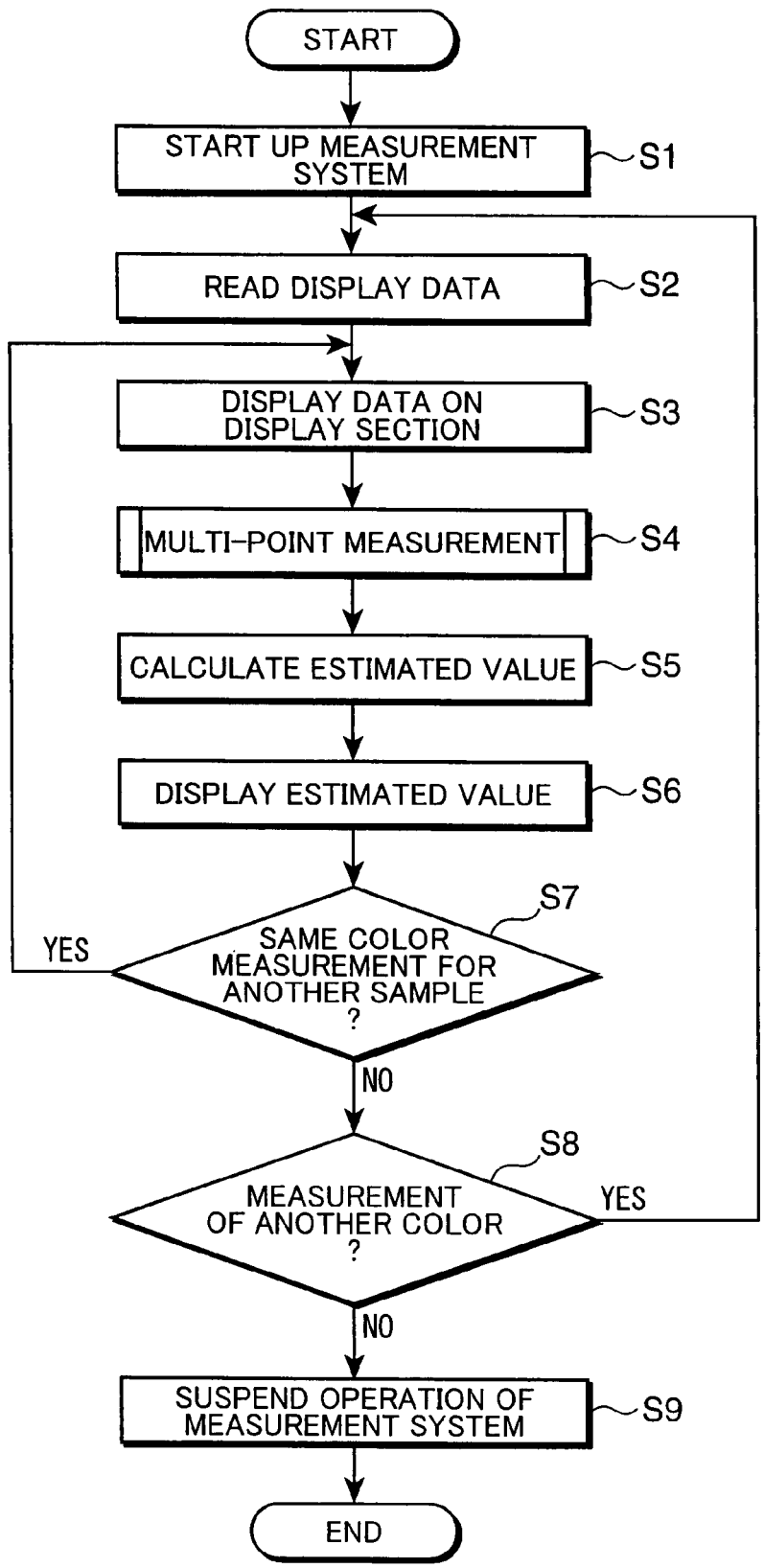
FIG. 9 is a flowchart showing an overall flow to be executed by the measurement system.

Now, an operation of the measurement system S having the above arrangement in the embodiment is described. FIG. 9 is a flowchart showing an overall flow to be executed by the measurement system S. When the measurement system S is started up (Step S1), the display controller 31 is operative to read image data from the display data storage 411 (Step S2). Then, the measurement navigation screen 50 as shown in FIG. 5 is displayed on the display section 13 (Step S3). Then, color measurement for the first through the sixth measurement areas R1 through R6 of the sample 21 is performed by the spectrophotometer 2 in the measurement order determined by the operator (Step S4). The operation flow in Step S4 will be described later in detail referring to FIG. 10.

After the measurement data for the first through the sixth measurement areas R1 through R6 are acquired, the computation processor 33 performs computation to obtain an estimated value (Step S5). The computation result is displayed on the display section 13 (Step S6). In this embodiment, an absorption coefficient ratio, a scattering coefficient ratio, and a K/S ratio are displayed in the respective columns (see FIG. 5) on the estimated value display portion 53.

Thereafter, it is confirmed whether the same color measurement is to be performed for another sample (Step S7). The judgment as to whether the same color measurement is to be performed depends on the command to be issued from the operating section 12. If a command indicating that the same color measurement is to be performed is issued from the operating section 12 (YES in Step S7), the routine returns to Step S3 to repeat the aforementioned operations. If, on the other hand, the same color measurement is not to be performed (NO in Step S7), it is confirmed whether measurement of another color is to be performed (Step S8).

If a command indicating that measurement of another color is to be performed is issued from the operating section 12 (YES in Step S8), the routine returns to Step S2 to repeat the operation that the display controller 31 reads image data corresponding to measurement of another color from the display data storage 411, and that the image data is displayed on the display section 13. If, on the other hand, measurement of another color is not to be performed (NO in Step S8), the operation of the measurement system S is suspended (Step S9), and the routine is ended.

Figure 10:
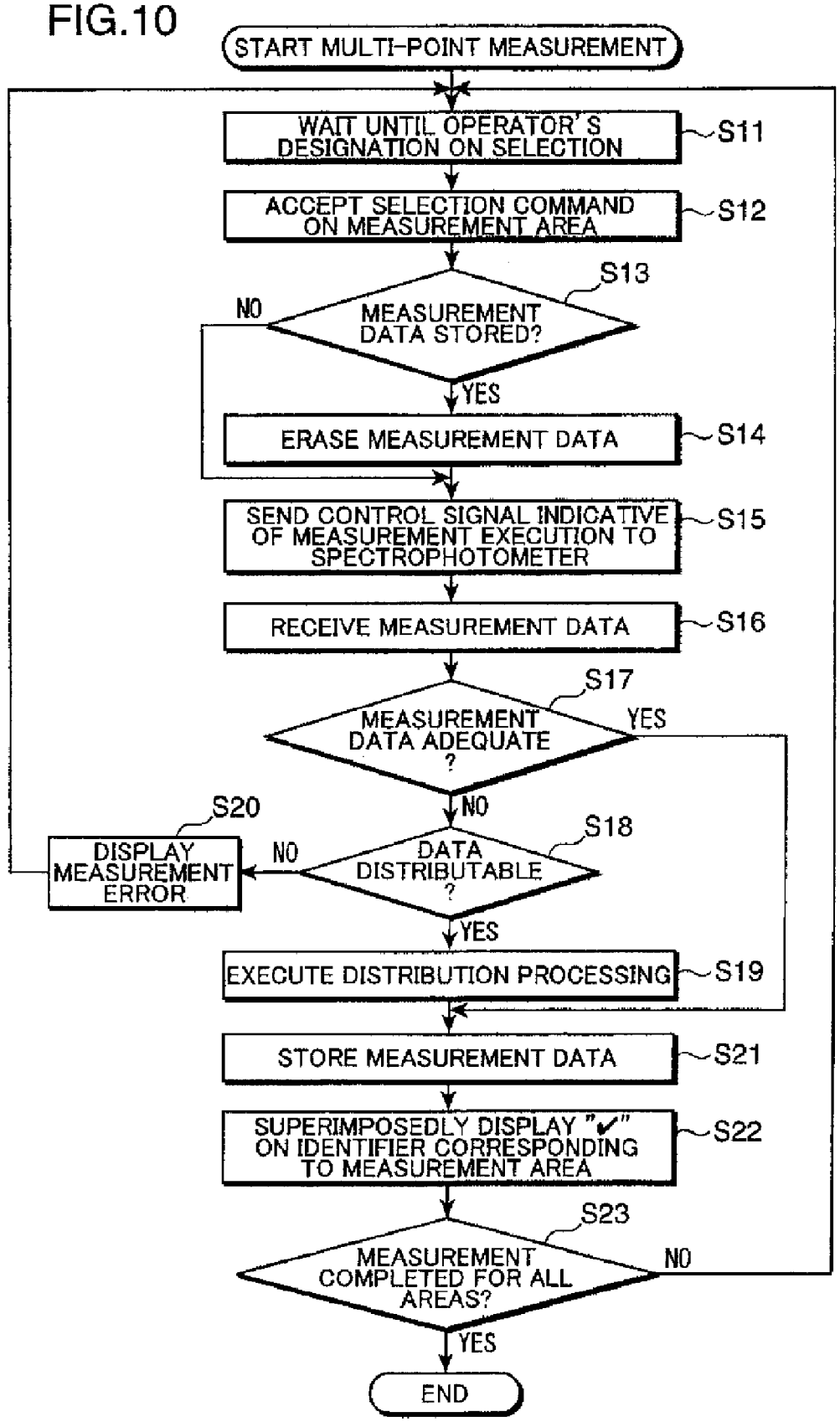
FIG. 10 is a flowchart showing a detailed flow on multi-point measurement in Step S4 in FIG. 9.

FIG. 10 is a flowchart showing a detailed flow on multipoint measurement in Step S4 shown in FIG. 9. The measurement system S waits for a selection command from the operator in a state that the measurement navigation screen 50 is displayed on the display section 13 (Step S11). In this condition, the operator directs the measurement aperture 2a of the spectrophotometer 2 to such a position as to oppose to an intended measurement site of the sample 21 corresponding to one of the first through the sixth measurement areas R1 through R6. Then, the operator points the measurement area on the measurement object image 510 corresponding to the intended measurement site of the sample 21 opposing the measurement aperture 2a with the mouse pointer, and clicks thereon. The clicking operation is accepted as a command indicating that color measurement for the selected measurement area is started by the measurement controller 32 (Step S12).

In response to receiving the command, the data arranger 35 checks whether the measurement data corresponding to the selected measurement area is stored in the measurement data storage 412 (Step S13). If it is judged that the measurement data is stored (YES in Step S13), the data arranger 35 erases the measurement data from the measurement data storage 412 (Step S14). If it is judged that the measurement data is not stored (NO in Step S13), the routine skips Step S14.

Thereafter, the measurement controller 32 sends a control signal requesting the spectrophotometer 2 to perform a measuring operation. In response to receiving the control signal, the spectrophotometer 2 performs color measurement for the selected measurement site of the sample 21 (Step S15). Then, measurement data i.e. spectral reflectance measurement data acquired by the measurement is received by the measurement controller 32 (Step S16).

Subsequently, the data distributor 36 compares the acquired measurement data with the distribution reference value stored in the reference value storage 413, and checks adequacy of the measurement data (Step S17). If it is judged that the measurement data is adequate by referring to the distribution reference value (YES in Step S17), the measurement data is stored in the measurement data storage 412 in association with the selected measurement area (Step S21).

If, on the other hand, it is judged that the measurement data is not adequate (NO in Step S17), the data distributor 36 judges whether the measurement data is distributable to other measurement area (Step S18). If it is judged that the measurement data is distributable to other measurement area (YES in Step S18), the data distributor 36 performs distribution processing of revising the identification information to be attached to the measurement data in such a form that the revised identification information identifies the measurement area to which the measurement data is distributed (Step S19). Thereafter, the measurement data is stored in the measurement data storage 412 (Step S21). If, it is judged that distribution is impossible (NO in Step S18), the data distributor 36 causes the display section 13 to display an error message (Step S20), and the routine returns to Step S11. In other words, the operator is prompted to perform measurement again.

Thereafter, the measurement controller 32 causes the discernible indicator to be displayed in association with the measurement area for which the measurement has been completed to display that the measurement has been completed (Step S22). Specifically, the measurement controller 32 is operative to superimposedly display the check mark "✓" as additive information on the corresponding one of the discernible indicators N1 through N6 (see FIG. 7). Then, the measurement data checker 34 judges whether a predetermined number of measurement data required for computation have been acquired in obtaining an estimated value by the computation processor 33 (Step S23). If the required number of measurement data have not been acquired (NO in Step S23), the routine returns to Step S11 to repeat the operations. If, on the other hand, the required number of measurement data have been acquired (YES in Step S23), the measurement data checker 34 causes the computation processor 33 to perform computation to obtain an estimated value (Step S5).

Figure 11A:
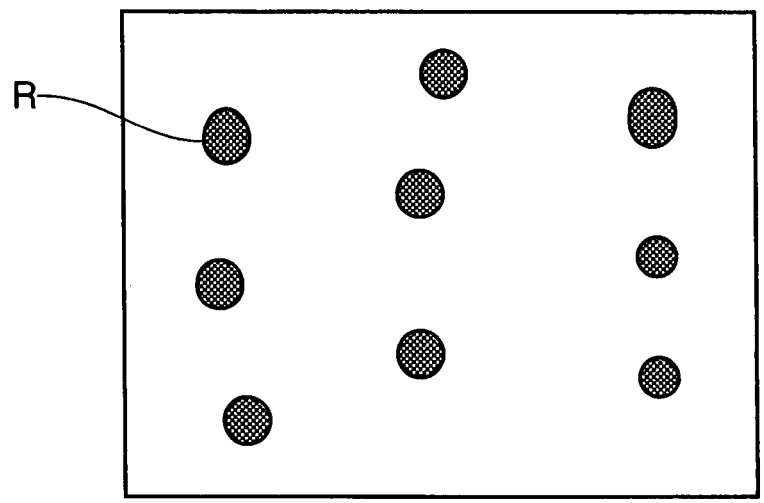
FIGS. 11A through 11C are diagrams for describing measurement latitude in applying the invention.
Figure 11B:
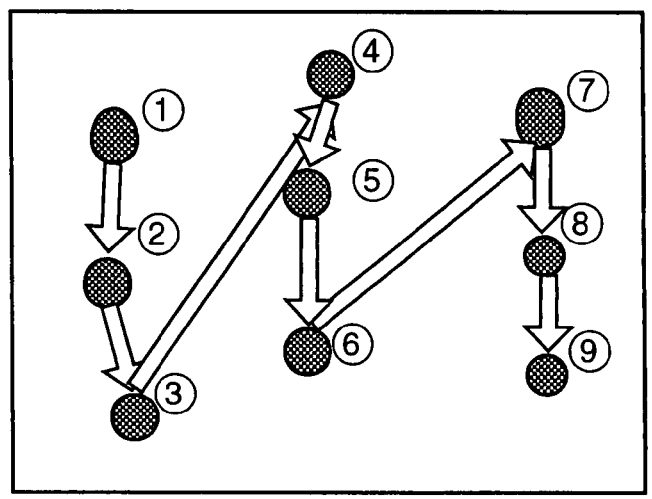
Figure 11C:
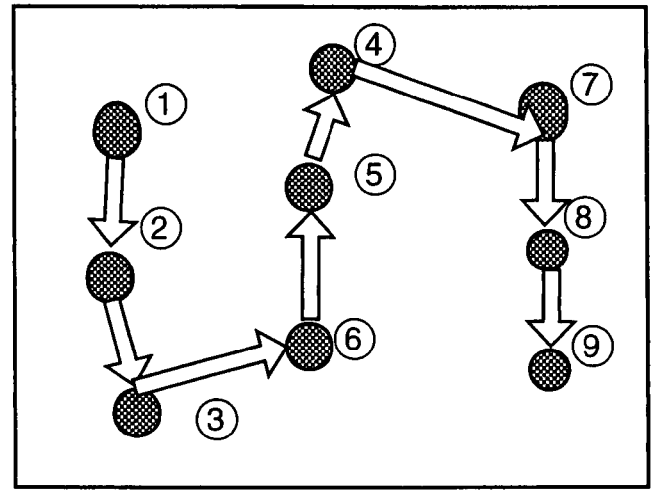

With use of the measurement system S having the above arrangement, the operator is allowed to flexibly set the measurement order according to his or her convenience, while securing measurement latitude, in performing a measuring operation of acquiring a required number of measurement data and obtaining a predetermined estimated value with use of the acquired multiple measurement data. For instance, as shown in FIG. 11A, if there exist multiple measurement areas R, there is a case that the measurement areas R are automatically numbered from the uppermost left position in the order as shown in FIG. 11B and that the measurement is navigated in the ascending order indicated by the encircled numbers. In this case, the moving amount from the measurement area indicated by the encircled number 3 to the measurement area indicated by the encircled number 4, or the moving amount from the measurement area indicated by the encircled number 6 to the measurement area indicated by the encircled number 7 may be unduly increased, which may require an unduly long time in shifting the measurement site by the measuring device. For instance, the measuring device may be a microscope or a like device, which is moved by XY-table. Unlike the above arrangement, the measurement system S of the embodiment enables to perform sequential measurement on a route where the moving amount is minimized, as shown in FIG. 11C, for instance.

Further, in use of the measurement system S, the operator can check the progress of measurement by way of the discernible indicators N1 through N6, irrespective of the measurement order for the measurement elements. This enables to suppress duplicate measurements of the same measurement area, or measurement skip. Furthermore, since there is no need for the operator to record the measurement data by himself or herself, the operation efficiency can be enhanced. In addition to the advantages, the measurement data checker 34 causes the computation processor 33 to perform computation of automatically obtaining an estimated value upon acquisition of the required number of measurement data in obtaining the estimated value. This enables to obtain the estimated value efficiently. Thus, the embodiment is advantageous in securely collecting measurement data required for obtaining an estimated value, and supporting the operator in efficiently obtaining the estimated value.

The embodiment of the invention is described as above. The invention is not limited to the foregoing, but may be modified as follows, for instance.

Figure 12:
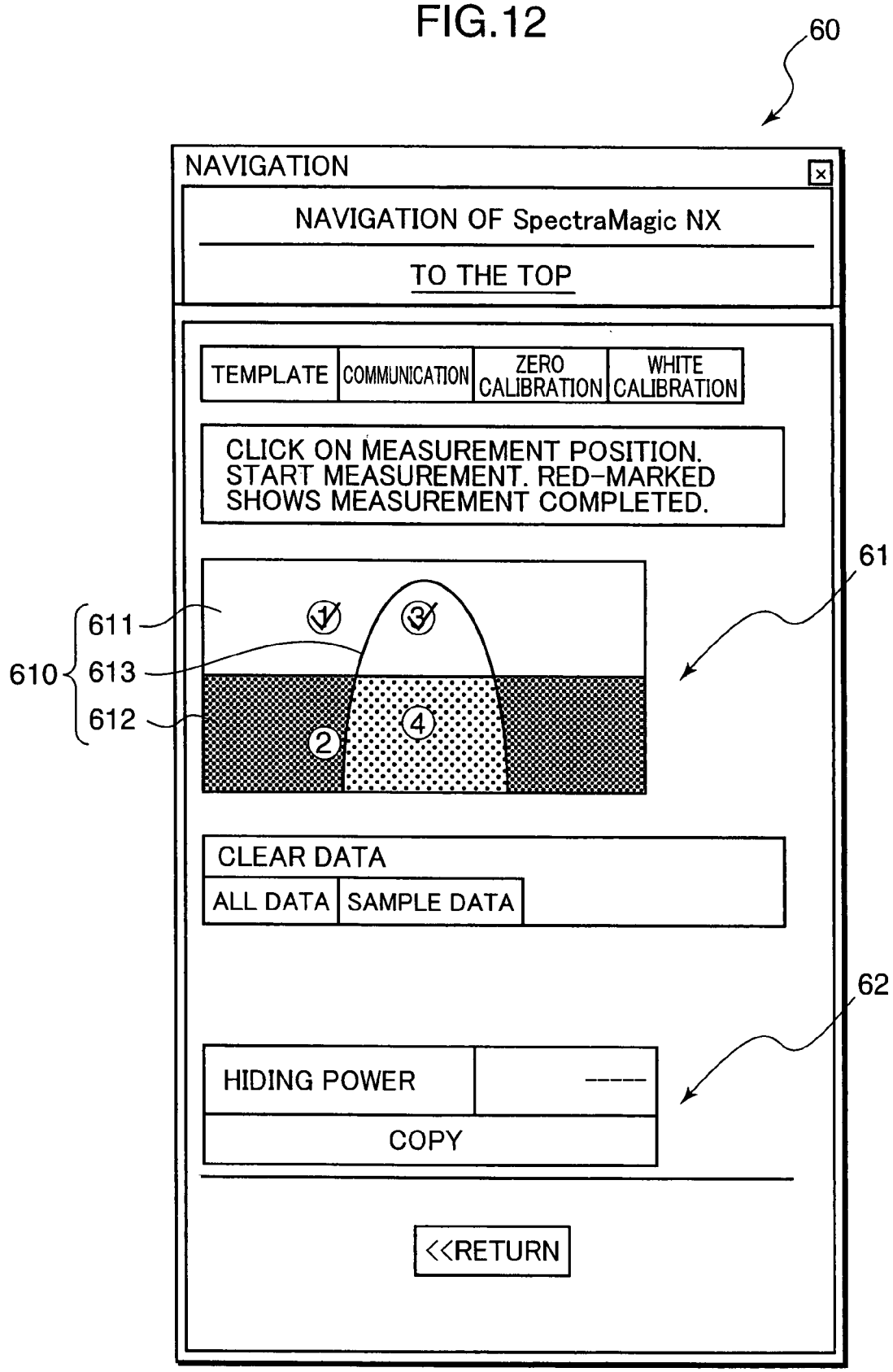
FIG. 12 is a plan view showing a measurement navigation screen, as an another example of the screen image to be displayed on the display section.

(1) In the embodiment, an absorption coefficient ratio, a scattering coefficient ratio, and a K/S ratio are obtained as the estimated value. Alternatively, the invention may be applied to an arrangement, in which e.g. the hiding power of a paint is obtained as the estimated value. FIG. 12 is a plan view showing a measurement navigation screen 60 to be displayed on the display section 13 by the display controller 31 for assessing the hiding power. The measurement navigation screen 60 includes a graphic display portion 61 and an estimated value display portion 62. The graphic display portion 61 has a white portion 611 corresponding to a white background portion, a black portion 612 corresponding to a black background portion, and a coated portion 613 corresponding to a coated layer of a sample paint. A measurement object image 610 in which the contours defining the white portion 611, the black portion 612, and the coated portion 613 are visually recognized is displayed on the graphic display portion 61.

With the above indication control, the measurement object image 610 is visually divided into four measurement areas. Discernible indicators indicated by encircled numbers are displayed in association with the four measurement areas, respectively. Each of the four measurement areas may function as a site for accepting a command indicating start for color measurement of the corresponding measurement area. Similarly to the embodiment, the measurement system S may be configured in such a manner that the hiding power of a paint is conclusively obtained as an estimated value.

(2) In the embodiment, the measurement object is an article including areas with different chromatic characteristics e.g. the sample 21 shown in FIG. 2, and the measuring device is the spectrophotometer 2. Alternatively, the invention may be applied to various arrangements, in which a measuring device capable of measuring distance-related parameters such as length, thickness, or diameter, parameters relating to temperature or humidity, optical parameters such as brightness, luminance, luminosity, refractive index, or transparency, shape-related parameters such as degree of surface coarseness, degree of surface curvature, depth of groove, and parameters relating to physical properties of liquid, solid, or gas is used, and a predetermined estimated value is obtained by using the parameters acquired by the measuring device.

Figure 13:
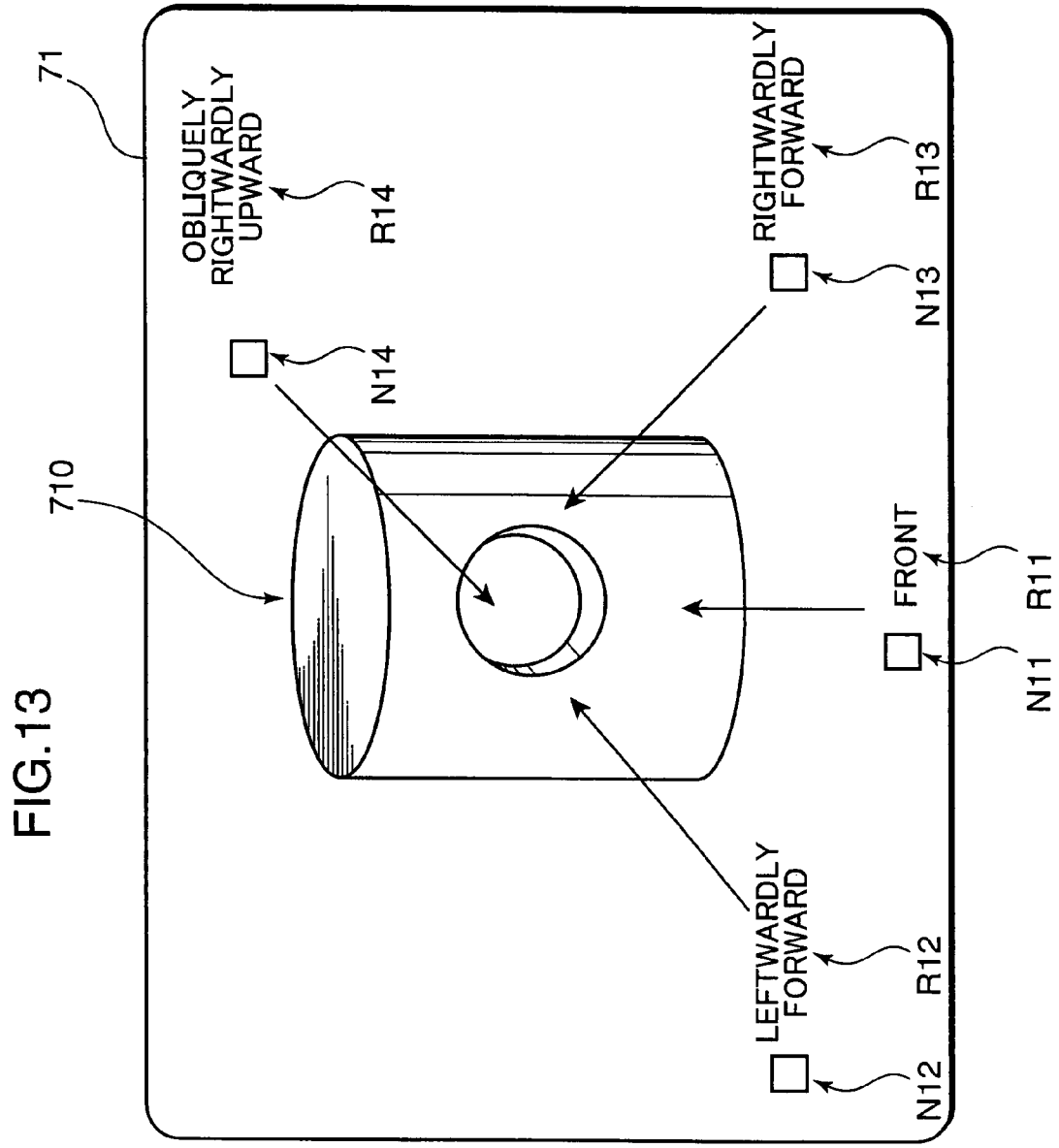
FIG. 13 is a plan view showing a modification of selection information.

(3) In the embodiment, the divided areas on the image of the sample 21 serve as selection information. Alternatively, the selection information may be obtained by displaying a button image describing the measurement contents in association with the measurement object image. FIG. 13 is a diagram showing the modification. Specifically, FIG. 13 is a plan view showing an example of an image to be displayed on a graphic display portion 71 of a measurement navigation screen to be displayed on the display section 13 in the case where the measurement object is an article with a stereoscopic configuration, and the measuring section is a three-dimensional shape measuring device.

There are displayed, on the graphic display portion 71, an image 710 of a measurement object, whose three-dimensional shape is to be measured, and which has a cylindrical shape with a hollow portion; button image portions R11, R12, R13, and R14 which include messages "FRONT", "LEFTWARDLY FORWARD", "RIGHTWARDLY FORWARD", and "OBLIQUELY RIGHTWARDLY UPWARD" describing measurement angles by the three-dimensional shape measuring device, and which function as sites for accepting a command indicating start of three-dimensional shape measurement at the designated measurement angle, respectively;

and discernible indicators N11, N12, N13, and N14 constituted of checkbox images to be displayed in association with the button image portions R11, R12, R13, and R14, respectively. In this arrangement, when the operator places the three-dimensional shape measuring device in front of the cylindrical measurement object, and clicks on the button image portion R11 describing "FRONT", the operator is allowed to measure the three-dimensional shape of the measurement object at the designated measurement angle corresponding to "FRONT". Upon completion of the measurement at the designated measurement angle, a check mark "✓" is attached to the discernible indicator N11.

Figure 14A:
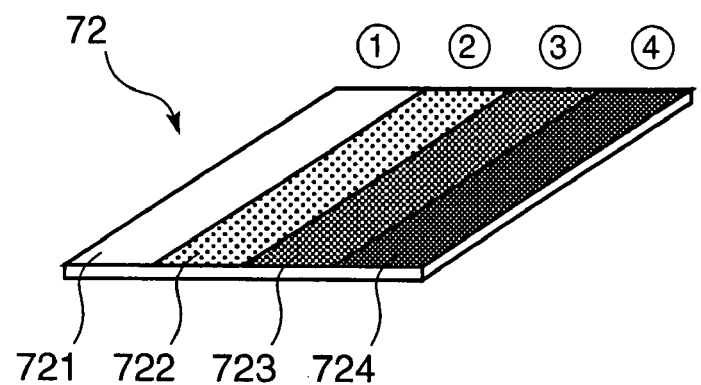
FIGS. 14A through 14C are diagrams showing further examples in calculating an estimated value by applying the invention.
Figure 14B:
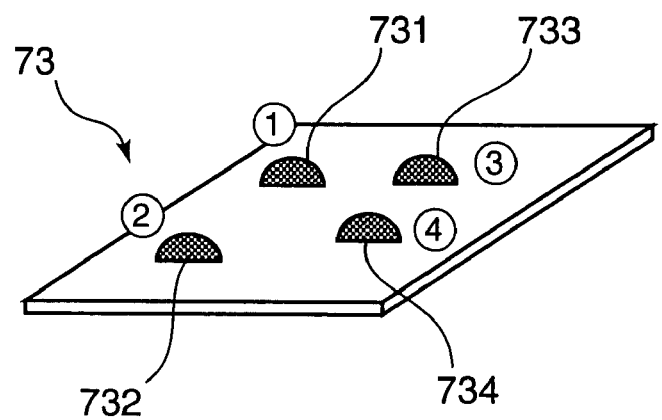
Figure 14C:
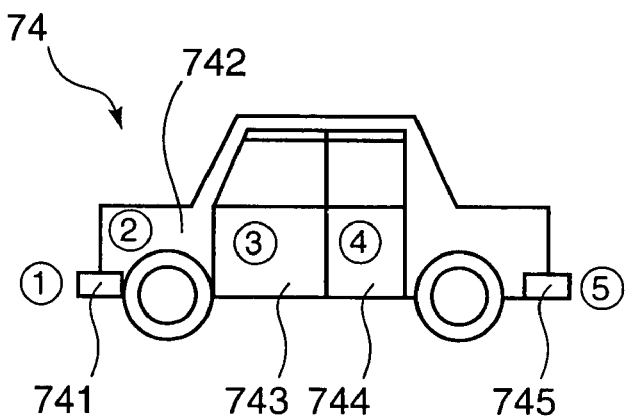

(4) FIGS. 14A through 14C are diagrams showing further modifications in applying the invention to obtain an estimated value. FIG. 14A shows a measurement sample 72, in which four different color strip-shaped patches 721, 722, 723, and 724 are arrayed on a base plate. With use of the measurement sample 72, a light resistance value of a paint sample, or an ICC profile of a printer or a like device may be obtained as an estimated value.

FIG. 14B shows a measurement sample 73, in which plural protrusions 731, 732, 733, and 734 are formed on a base plate. With use of the measurement sample 73, and a CCD area sensor or a like device as the measuring device, for instance, an estimated value of the size of a soldered portion of a circuit board may be obtained. Likewise, an estimated value relating to the magnitude of a flaw of a painted board, a color filter, a glass plate, or a like member may be obtained.

FIG. 14C shows an example, in which the entirety of an automobile serves as a measurement sample 74. In this case, for instance, a front bumper 741, a bonnet 742, a front door 743, a rear door 744, and a rear bumper 745 serve as measurement areas, and a color difference among the measurement areas may be obtained as an estimated value. The invention is applicable to such a large-sized sample, as well as the foregoing samples.

(5) It is possible to provide an operation program of executing a process to be executed by the measurement system S, as a modified embodiment to carry out the invention, in place of the measurement system S. The program may be provided as a program product by recording the program in a computer-readable recording medium, which is an attachment to a computer, such as a flexible disk, a CD-ROM, an ROM, an RAM, or a memory card. Also, the program may be provided by recording the program in an ROM 42 equipped in the personal computer shown in FIG. 3. Further, the program may be provided by downloading via a network.

The aforementioned embodiment and/or modifications primarily include the inventions having the following arrangements.

A measurement system according to an aspect of the invention is a measurement system for obtaining a predetermined estimated value by using multiple measurement data. The measurement system includes: a measuring section for performing a predetermined measurement with respect to a measurement object to acquire measurement data; a display section for displaying indication concerning a measurement; a display controller for causing the display section to display first information relating to a plurality of measurement elements of the measurement object required for acquiring the multiple measurement data, the first information including individual selection information relating to the measurement elements; and second information to be displayed in association with the selection information for allowing an operator to recognize whether measurement of the corresponding measurement element has been completed; a measurement controller for performing a measurement start control of causing the individual selection information to function as a site for accepting a command indicating start of the measurement of the corresponding measurement element relating to the individual selection information; a measurement execution control of causing the measuring section to perform the measurement of the selected measurement element; and a measurement completion display control of causing the display section to display whether the measurement has been completed in association with the selection information; a storing section for storing the measurement data acquired by the measurement in association with the measurement element; a computing section for reading the multiple measurement data from the storing section to compute the estimated value; and a checking section for checking whether the measurement data required for the computation has been acquired in computing the estimated value by the computing section.

In the above arrangement, since the selection information individually indicating the measurement elements is displayed on the display section, the operator can grasp the entirety of the measurement elements. Also, the selection information functions as the site for accepting the command indicating start of the measurement, and the measurement completion indication is displayed with respect to the measurement element for which the measurement has been completed. This allows the operator to grasp the progress of the measuring operation for the individual measurement elements. Since the operator can check the progress of measurement, irrespective of the measurement order of the measurement elements, this arrangement enables to suppress duplicate measurements of the same measurement element, or measurement skip.

Also, the measurement data acquired by the measurement is stored in the storing section in association with the information for specifying the measurement element. Accordingly, there is no need for the operator to record the measurement data by himself or herself. Further, since the checking section is provided to check whether the certain number of measurement data required for computation in obtaining the estimated value have been acquired, the computing section is allowed to perform computation of automatically obtaining the estimated value upon acquisition of the measurement data required for obtaining the estimated value.

In the above arrangement, preferably, the display controller may be operative to display image information representing an image of the measurement object, or an image simulating the measurement object in displaying the first information; and the first information and the second information may be displayed in correspondence to the image information.

The above arrangement enables to provide the operator with user-friendly indication.

In the above arrangement, preferably, the selection information may be constituted of a plurality of areas of the image of the measurement object for which the measurement is to be performed, the areas being obtained by visually dividing the measurement object image as the measurement elements, and the measurement controller may perform the measurement start control in such a manner that each of the areas of the measurement object image to be displayed on the display section is functioned as a site for accepting a command indicating start of the measurement of the corresponding area.

In the above arrangement, in response to the operator's selection of a measurement area for which the measurement is to be performed, on the image representing the measurement object to be displayed on the display section, the measurement for the measurement area can be executed. Also, the measurement completion indication is displayed in association with the measurement area. Thereby, the operator is allowed to perform the measuring operation while clearly and visually recognizing the measurement area and the progress of measurement to be displayed on the measurement object image. This allows the operator to perform the measuring operation accurately and efficiently.

In the above arrangement, preferably, the second information may include one or more identifiers selected from the group consisting of at least numerals, characters, symbols, and pictograms, the second information being allocated in correspondence to the selection information, and the measurement controller may perform the measurement completion display control in such a manner that predetermined additive information is superimposedly displayed on the identifier.

In the above arrangement, user-friendly indication is performed in such a manner that everyone can easily comprehend by e.g. setting a serial number or a checkbox individually allocated to the measurement elements i.e. the selection information as an indicator of the second information, and superimposedly displaying a check mark "✓" on the corresponding number or checkbox upon completion of the measurement.

In the above arrangement, preferably, the measurement system may further include a selector for issuing the command of starting the measurement with respect to each of the measurement elements. This arrangement enables to easily give the command indicating start of the measurement to the measurement element i.e. the selection information by the selector such as a mouse.

In the above arrangement, preferably, the measurement system may further include: a data arranger for selectively erasing the measurement data from the storing section, wherein the data arranger is operative to erase the measurement data that has been acquired in relation to the measurement element from the storing section in response to issuance of a predetermined operation command to the selection information displayed on the display section, and the measurement controller is operative to change a measurement completion indication to be displayed in association with the selection information corresponding to the erased measurement element into a measurement incompletion indication.

In the above arrangement, in the case where measurement objects of the same configuration are sequentially measured multiple times, in response to issuance of an operation command to certain selection information i.e. a measurement element of the measurement object to be measured next, which corresponds to the measurement element of the previously-measured measurement object, the measurement data of the measurement element of the previously-measured measurement object is erased from the storing section. Further, the measurement completion indication at the measurement element of the measurement object to be measured next is changed into a measurement incompletion indication. This eliminates a drawback that the measurement data of the previously-measured measurement object may be used in obtaining an estimated value for the measurement object to be measured next. Thereby, there is no need for the operator to reset the measurement data or discernible indication.

In the above arrangement, preferably, the data arranger may be operable to read correlation information representing that a first measurement element and one or more second measurement elements different from the first measurement element are correlated with each other, and the data arranger may be operative to erase the measurement data that has been acquired in relation to the first measurement element and the second measurement element or elements in response to issuance of the operation command to the selection information corresponding to the first measurement element.

In the case where measurement objects of the same configuration are sequentially measured multiple times, concerning some groups of measurement elements, measurement may be performed with respect to a single measurement object by commonly using the measurement objects. However, concerning other groups of measurement elements, it may be necessary to perform measurement with respect to individual measurement objects. In the above arrangement, in response to issuance of an operation command to any one of the measurement elements in the latter group, the measurement data of the other measurement elements which belong to the same group and which have been acquired in the previous measurement are erased from the storing section, as well as the measurement data of the designated measurement element. This enables to further enhance the operation efficiency.

In the above arrangement, preferably, the measurement system may further include: a reference value storage for storing a range of values of the measurement data which is supposed to be acquired with respect to each of the measurement elements, as a distribution reference value; and a determining section for determining the measurement element corresponding to the measurement data acquired by the measuring section, based on the distribution reference value.

In the above arrangement, in the case where the measurement element on the image information, whose measurement is designated by the operator, and the measurement element actually measured by the measuring section are not coincident, the determining section determines the measurement element from which the measurement data has been derived by the actual measurement, based on the distribution reference value. This enables to prevent likelihood that the measurement data may be stored in the storing section in association with the measurement element that should not be associated with the measurement data.

In the above arrangement, preferably, the measurement system may further include a casing member for accommodating the measuring section, the display section, the display controller, the measurement controller, the storing section, the computing section, and the checking section therein.

In the above arrangement, since the measurement system can be provided in such a manner that the components of the measurement system are integrally mounted in the casing member, the measurement system is provided with superior handling performance or portability.

In the above arrangement, preferably, the measurement object may be an article including a plurality of areas having chromatic characteristics different from each other, and the measuring section may be a spectrophotometer for measuring the color of the article. As another preferred arrangement, the measurement object may be an article with a stereoscopic configuration, and the measuring section may be a three-dimensional shape measuring device for measuring the three-dimensional shape of the article.

A measurement system according to another aspect of the invention is a measurement system for obtaining a predetermined estimated value by using multiple measurement data. The measurement system includes: a measuring section for performing a predetermined measurement with respect to a measurement object to acquire measurement data; a display section for displaying navigating information; a display controller for causing the display section to display image information representing an image of the measurement object or an image simulating the measurement object image, area information for use in visually dividing the measurement object image into a certain number of measurement areas required for acquiring the multiple measurement data, and identification information for allowing an operator to recognize whether a targeted site of the measurement object for the measurement has been selected in correspondence to the measurement area; a selector for accepting selection of the targeted site of the measurement object in the unit of measurement areas on the display section; a measurement controller for performing a measurement start control of functioning the selection by the selector as a command indicating start of the measurement; and a measurement execution control of causing the measuring section to perform the measurement of the selected measurement area; a storing section for storing the measurement data acquired by the measurement in association with the measurement area; a computing section for reading the multiple data from the storing section to compute the estimated value; and a checking section for checking whether the measurement data required for the computation has been acquired in computing the estimated value by the computing section.

A program product according to yet another aspect of the invention is a program product for operating a measurement system, provided with a display section, a storing section, and a data processor, to obtain a predetermined estimated value by performing a predetermined measurement with respect to a measurement object and using a required number of measurement data acquired by the measurement. The program product includes: a program which causes the data processor to execute: a process of causing the display section to display image information representing an image of the measurement object in a state that selection information for allowing an operator to visually recognize a plurality of measurement elements of the measurement object for which the measurement is to be performed is included, and display a discernible indicator, to be displayed in association with the selection information, for allowing the operator to recognize whether the measurement has been completed; a process of functioning each of the selection information to be displayed on the display section as a site for accepting a command indicating start of the measurement of the corresponding measurement element relating to the individual selection information, and generating a command signal to cause a measuring section to perform the measurement in response to receiving the command; a process of causing the discernible indicator of the measurement element for which the measurement has been completed to display that the measurement has been completed; a process of causing the storing section to store the measurement data acquired by the measurement in association with information for specifying the measurement element; a process of reading the measurement data from the storing section to perform computation to obtain the estimated value; a process of determining whether a predetermined number of measurement data required for the computation has been acquired in obtaining the estimated value; and a process of causing the display section to display the estimated value obtained by the computation; and a medium for recording the program.

According to the arrangements of the invention, in performing a measuring operation of acquiring a required number of measurement data and obtaining a predetermined estimated value by using the multiple measurement data, the operator can check the progress of measurement irrespective of the measurement order of the measurement elements. This enables to suppress duplicate measurements of the same measurement element, or measurement skip. Thus, the operator is allowed to flexibly set the measurement order according to his or her convenience, while securing measurement latitude, and prevent measurement error. Further, since there is no need for the operator to record the measurement data by himself or herself, the operation efficiency can be enhanced. In addition to the above advantages, the computing section is allowed to perform computation of automatically obtaining an estimated value upon acquisition of a certain number of measurement data required for obtaining the estimated value. This enables to obtain the estimated value efficiently. Thus, the above arrangements of the invention are advantageous in providing a measurement system that enables to securely collect measurement data required for obtaining an estimated value while preventing measurement error, and support the operator in efficiently obtaining the estimated value, as well as a program product for operating the measurement system.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A measurement system for obtaining a predetermined estimated value by using multiple measurement data, the measurement system comprising:

a measuring section for performing a predetermined measurement with respect to a measurement object to acquire measurement data;

a display section for displaying indication concerning a measurement;

a display controller for causing the display section to display:

first information relating to a plurality of measurement elements of the measurement object required for acquiring the multiple measurement data, the first information including individual selection information relating to the measurement elements, said individual selection information being constituted of a plurality of areas of the image of the measurement object for which the measurement is to be performed, the areas being obtained by visually dividing the measurement object image into the measurement elements; and second information to be displayed in association with the selection information for allowing an operator to recognize whether measurement of the corresponding measurement element has been completed;

a measurement controller for performing:

a measurement start control of causing the individual selection information to function as a site for accepting a command from an operator indicating the start of the measurement of the corresponding measurement element relating to the individual selection information, said command initiated by an operator using the display by choosing the individual selection information that corresponds to an area of the image of the measurement object for which measurement is to be performed;

a measurement execution control of causing the measuring section to perform the measurement of the selected measurement element in response to said command; and a measurement completion display control of causing the display section to display whether the measurement has been completed in association with the selection information;

a storing section for storing the measurement data acquired by the measurement in association with the measurement element;

a computing section for reading the multiple measurement data from the storing section to compute the estimated value; and a checking section for checking whether the measurement data required for the computation has been acquired in computing the estimated value by the computing section.

2. The measurement system according to claim 1, wherein the display controller is operative to display image information representing an image of the measurement object, or an image simulating the measurement object in displaying the first information; and the first information and the second information are displayed in correspondence to the image information.

3. The measurement system according to claim 2, wherein the measurement controller performs the measurement start control in such a manner that each of the areas of the measurement object image to be displayed on the display section is functioned as a site for accepting a command indicating start of the measurement of the corresponding area.

4. The measurement system according to claim 1, wherein the second information includes one or more identifiers selected from the group consisting of at least numerals, characters, symbols, and pictograms, the second information being allocated in correspondence to the selection information, and the measurement controller performs the measurement completion display control in such a manner that predetermined additive information is superimposedly displayed on the identifier.

5. The measurement system according to claim 1, further comprising:

a selector for issuing the command of starting the measurement with respect to each of the measurement elements.

6. The measurement system according to claim 1, further comprising:

a data arranger for selectively erasing the measurement data from the storing section, wherein the data arranger is operative to erase the measurement data that has been acquired in relation to the measurement element from the storing section in response to issuance of a predetermined operation command to the selection information displayed on the display section, and the measurement controller is operative to change a measurement completion indication to be displayed in association with the selection information corresponding to the erased measurement element into a measurement incompletion indication.

7. The measurement system according to claim 6, wherein the data arranger is operable to read correlation information representing that a first measurement element and one or more second measurement elements different from the first measurement element are correlated with each other, and the data arranger is operative to erase the measurement data that has been acquired in relation to the first measurement element and the second measurement element or elements in response to issuance of the operation command to the selection information corresponding to the first measurement element.

8. The measurement system according to claim 1, further comprising:

a reference value storage for storing a range of values of the measurement data which is supposed to be acquired with respect to each of the measurement elements, as a distribution reference value; and a determining section for determining the measurement element corresponding to the measurement data acquired by the measuring section, based on the distribution reference value.

9. The measurement system according to claim 1, further comprising:

a casing member for accommodating the measuring section, the display section, the display controller, the measurement controller, the storing section, the computing section, and the checking section therein.

10. The measurement system according to claim 1, wherein the measurement object is an article including a plurality of areas having chromatic characteristics different from each other, and the measuring section is a spectrophotometer for measuring the color of the article.

11. The measurement system according to claim 1, wherein the measurement object is an article with a stereoscopic configuration, and the measuring section is a three-dimensional shape measuring device for measuring the three-dimensional shape of the article.

12. A measurement system for obtaining a predetermined estimated value by using multiple measurement data, the measurement system comprising:

a measuring section for performing a predetermined measurement with respect to a measurement object to acquire measurement data;

a display section for displaying navigating information;

a display controller for causing the display section to display:

image information representing an image of the measurement object or an image simulating the measurement object image;

area information for use in visually dividing the measurement object image into a certain number of measurement areas required for acquiring the multiple measurement data; and identification information for allowing an operator to recognize whether a targeted site of the measurement object for the measurement has been selected in correspondence to the measurement area;

a selector for accepting selection from an operator of the targeted site of the measurement object in the unit of measurement areas on the display section;

a measurement controller for performing:

a measurement start control of functioning the selection by the selector as a command indicating start of the measurement; and a measurement execution control of causing the measuring section to perform the measurement of the selected measurement area in response to said command;

a storing section for storing the measurement data acquired by the measurement in association with the measurement area;

a computing section for reading the multiple data from the storing section to compute the estimated value; and a checking section for checking whether the measurement data required for the computation has been acquired in computing the estimated value by the computing section.

13. A computer program product stored on a tangible medium containing instructions executable by a computer for operating a measurement system, said computer being provided with a display section, a storing section, and a data processor, said instructions stored on said computer program product being configured, when executed by a computer, to obtain a predetermined estimated value by making the computer perform a process comprising the steps of:

causing the display section to display image information representing an image of the measurement object in a state that selection information for allowing an operator to visually recognize a plurality of measurement elements of the measurement object for which the measurement is to be performed is included, and display a discernible indicator, to be displayed in association with the selection information, for allowing the operator to recognize whether the measurement has been completed;

causing each of the selection information to be displayed on the display section as a site for accepting a command from an operator indicating start of the measurement of the corresponding measurement element relating to the individual selection information, and generating a control signal to cause a measuring section to perform the measurement in response to receiving the command;

causing the discernible indicator of the measurement element for which the measurement has been completed to display that the measurement has been completed;

causing the storing section to store the measurement data acquired by the measurement in association with information for specifying the measurement element;

reading the measurement data from the storing section to perform a computation to obtain the estimated value;

determining whether a predetermined number of measurement data required for the computation has been acquired in obtaining the estimated value; and causing the display section to display the estimated value obtained by the computation.

14. A computer system for operating a measurement system, said computer system including a display, a memory, and a processor, said computer system being configured to obtain a predetermined estimated value of a measurement object as a result of said processor being programmed to execute the following steps:

causing the display to display image information representing an image of the measurement object in a state that selection information for allowing an operator to visually recognize a plurality of measurement elements of the measurement object for which a measurement is to be performed is included, and display a discernible indicator, to be displayed in association with the selection information, for allowing the operator to recognize whether the measurement has been completed;

causing each of the selection information to be displayed on the display as a site for accepting a command from an operator indicating start of the measurement of the corresponding measurement element relating to the individual selection information, and generating a control signal to cause a measuring section to perform the measurement in response to receiving the command;

causing the discernible indicator of the measurement element for which the measurement has been completed to display that the measurement has been completed;

causing the memory to store the measurement data acquired by the measurement in association with information for specifying the measurement element;

reading the measurement data from the memory to perform a computation to obtain the estimated value;

determining whether a predetermined number of measurement data required for the computation has been acquired in obtaining the estimated value; and causing the display to display the estimated value obtained by the computation.

* * * * *